(12) United States Patent
Pacetti et al.

(10) Patent No.: US 8,808,723 B2
(45) Date of Patent: *Aug. 19, 2014

(54) POLYMERS CONTAINING POLY(ESTER AMIDES) AND AGENTS FOR USE WITH MEDICAL ARTICLES AND METHODS OF FABRICATING THE SAME

(75) Inventors: Stephen D. Pacetti, San Jose, CA (US); Charles Claude, Sunnyvale, CA (US); Thierry Glauser, Redwood City, CA (US); Jessica R. DesNoyer, Santa Clara, CA (US); Syed F. A. Hossainy, Fremont, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 262 days.

This patent is subject to a terminal disclaimer.

(21) Appl. No.: 12/504,542

(22) Filed: Jul. 16, 2009

(65) Prior Publication Data

US 2009/0274741 A1     Nov. 5, 2009

Related U.S. Application Data

(63) Continuation of application No. 10/855,294, filed on May 26, 2004.

(51) Int. Cl.
    *C08G 69/44*    (2006.01)
    *A61L 31/10*    (2006.01)
    *A61L 27/34*    (2006.01)
    *A61L 29/08*    (2006.01)

(52) U.S. Cl.
    USPC .......................................... 424/423; 521/185

(58) Field of Classification Search
None
See application file for complete search history.

(56) References Cited

U.S. PATENT DOCUMENTS

| | | | |
|---|---|---|---|
| 4,368,090 A | 1/1983 | Mumcu et al. | |
| 4,483,975 A | 11/1984 | De Jong et al. | |
| 4,733,665 A | 3/1988 | Palmaz | |
| 4,800,882 A | 1/1989 | Gianturco | |
| 4,886,062 A | 12/1989 | Viktor | |
| 5,489,667 A | 2/1996 | Knipf et al. | |
| 5,509,899 A * | 4/1996 | Fan et al. ................ | 604/103.14 |
| 5,644,020 A | 7/1997 | Timmermann et al. | |
| 6,316,585 B1 | 11/2001 | Lele | |
| 6,420,045 B1 | 7/2002 | Faulhammer et al. | |
| 6,503,538 B1 | 1/2003 | Chu et al. | |
| 2004/0072857 A1 | 4/2004 | Waugh et al. | |

FOREIGN PATENT DOCUMENTS

| | | |
|---|---|---|
| EP | 0 583 888 | 2/1994 |
| GB | 1 137 209 | 12/1968 |
| JP | 63-277636 A | 11/1988 |
| JP | 04-103566 A | 4/1992 |

(Continued)

OTHER PUBLICATIONS

International Search Report for PCT/US2005/017690 filed May 18, 2005, mailed Dec. 1, 2005, 29 pgs.

(Continued)

*Primary Examiner* — Rachael E Bredefeld
(74) *Attorney, Agent, or Firm* — Squire Patton Boggs (US) LLP

(57) ABSTRACT

Polymers containing poly(ester amides) and agents for use with medical articles and methods of fabricating the same are disclosed. The medical article generally comprises an implantable substrate having a coating, and the coating contains a polymer comprising a polymeric product of a reaction comprising a polyol, a polycarboxylic acid, an amino acid and an agent.

13 Claims, 3 Drawing Sheets

(56) References Cited

FOREIGN PATENT DOCUMENTS

| WO | WO 02/18477 | | 3/2002 | |
| WO | WO03/062298 | * | 7/2003 | ............ C08G 63/00 |
| WO | WO 2005/061024 | | 7/2005 | |

OTHER PUBLICATIONS

Invitation to Pay Additional Fees of a PCT/US2005/017690 filed May 18, 2005, mailed Sep. 20, 2005, 7 pgs.

* cited by examiner

POLYMERS CONTAINING POLY(ESTER AMIDES) AND AGENTS FOR USE WITH MEDICAL ARTICLES AND METHODS OF FABRICATING THE SAME

CROSS-REFERENCE

This application is a continuation of U.S. application Ser. No. 10/855,294 filed on May 26, 2004, the teaching of which is incorporated by reference in its entirety.

BACKGROUND

1. Field of the Invention

This invention is directed to polymers for use with medical articles and, more specifically, polymers containing poly(ester amides) and agents.

2. Description of the State of the Art

A current paradigm in biomaterials research is the control of protein adsorption on an implant surface. Uncontrolled protein adsorption on an implant surface is a problem with current biomaterial implants and leads to a mixed layer of partially denatured proteins on the implant surface. This mixed layer of partially denatured proteins leads to disease, for example, by providing cell-binding sites from adsorbed plasma proteins such as fibrinogen and immunoglobulin G. Platelets and inflammatory cells such as, for example, monocytes, macrophages and neutrophils, adhere to the cell-binding sites. A wide variety of proinflammatory and proliferative factors may be secreted and result in a diseased state. Accordingly, a non-fouling surface, which is a surface which does not become fouled or becomes less fouled with this layer of partially denatured proteins, is desirable.

A stent is an example of an implant that can benefit from a non-fouling surface. Stents are a mechanical intervention that can be used as a vehicle for delivering pharmaceutically active agents. As a mechanical intervention, stents can physically hold open and, if desired, expand a passageway within a mammal. Typically, a stent may be compressed, inserted into a small vessel through a catheter, and then expanded to a larger diameter once placed in a proper location. Examples of patents disclosing stents include U.S. Pat. Nos. 4,733,665, 4,800,882 and 4,886,062.

Stents play an important role in a variety of medical procedures such as, for example, percutaneous transluminal coronary angioplasty (PTCA), which is a procedure used to treat heart disease. In PTCA, a balloon catheter is inserted through a brachial or femoral artery, positioned across a coronary artery occlusion, inflated to compress atherosclerotic plaque and open the lumen of the coronary artery, deflated and withdrawn. Problems with PTCA include formation of intimal flaps or torn arterial linings, both of which can create another occlusion in the lumen of the coronary artery. Moreover, thrombosis and restenosis may occur several months after the procedure and create a need for additional angioplasty or a surgical by-pass operation. Stents are generally implanted to reduce occlusions, inhibit thrombosis and restenosis, and maintain patency within vascular lumens such as the lumen of the coronary artery.

Local delivery of agents is often preferred over systemic delivery of agents, particularly where high systemic doses are necessary to achieve an effect at a particular site within a mammal, because high systemic doses of agent can often create adverse effects within the mammal. One proposed method of local delivery includes coating the surface of a medical article with a polymeric carrier and attaching an agent to the polymeric carrier. Some of the currently desired polymeric materials are biodegradable but, unfortunately, these polymers do not have sufficient mechanical properties for a number of medical applications. For example, the hardness of currently available poly(ester amides) has been found to be insufficient for many stent applications. Accordingly, there is a need for biodegradable polymeric materials with better mechanical properties.

Another problem involves regulatory concerns associated with the release of agents from biodegradable coatings within a mammal. The problem is that molecules from the polymeric carrier may be attached to the agent upon breakdown of the coating. Since these additional molecules were not considered in the original regulatory approval of the agent, there may be regulatory concerns over possible changes in the agent's biological activity. Accordingly, there is a need for coatings that release agents that are substantially free of additional molecules derived from a polymeric carrier.

SUMMARY

Embodiments of the present invention generally encompass polymers containing poly(ester amides) and agents such as therapeutic, prophylactic or other agents, for use with medical articles. Methods for fabricating those polymers are also encompassed by the present invention. In some embodiments, the polymers generally comprise a poly(ester amide) that is a polymeric product of a reaction between a polyol, a polycarboxylic acid, an amino acid, and an agent.

In some embodiments, the invention can include a polymer represented by a formula:

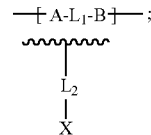

wherein A comprises

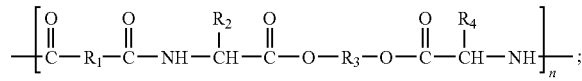

and B comprises

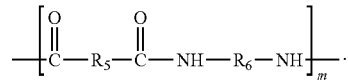

The groups $R_1$ and $R_5$ are optional and can be selected independently from substituted, unsubstituted, hetero-, straight-chained, branched, cyclic, saturated and unsaturated aliphatic radicals; and substituted, unsubstituted, and heteroaromatic radicals. The group $R_3$ can be selected from substituted, unsubstituted, hetero-, straight-chained, branched, cyclic, saturated and unsaturated aliphatic radicals; and substituted, unsubstituted, and hetero-aromatic radicals. The groups $R_2$ and $R_4$ can be independently selected from hydrogen; substituted, unsubstituted, hetero-, straight-chained, branched, cyclic, saturated and unsaturated aliphatic radicals; and substituted, unsubstituted, and hetero-aromatic radicals. The group $R_6$ can be selected from substituted, unsubstituted, hetero-, straight-chained and branched aliphatic radicals. The group $L_1$ can be an optional linkage connecting A to B, and the group X can be optionally an agent. The group $L_2$ can optionally be a linkage connecting X to the polymer, and n and m are integers not equal to 0. However, if (i) $R_1$, $R_3$ and $R_5$ are independently selected straight-chained or branched saturated aliphatic radicals having from 2-20 carbon atoms; (ii) $R_2$ and $R_4$ are independently selected straight-chained or branched saturated aliphatic radicals having from 1-6 carbon atoms, straight-chained or branched aliphatic radicals having from 2-6 carbon atoms and at least one unsaturated carbon-carbon bond, straight-chained or branched aliphatic radicals having from 2-6 carbon atoms and at least one carbon-carbon triple bond, phenyl radicals, an ortho-fused bicyclic carbocyclic radical having 6-10 carbon atoms and at least one aromatic ring, or hydrogen; (iii) $R_6$ is a pentylene radical; and, (iv) X is a straight-chained or branched saturated aliphatic radical having from 1-6 carbon atoms, a phenyl radical, an ortho-fused bicyclic carbocyclic radical having 6-10 carbon atoms and at least one aromatic ring, or hydrogen; and, (v) m and n are integers not equal to 0; then, $L_2$ cannot be

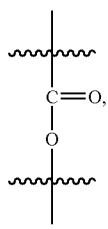 [SMILES: *OC(*)=O]

when the carbon of $L_2$ is attached to either $C_1$ or $C_5$ of the pentylene radical, $R_6$. Furthermore, if (i) $R_1$ and $R_5$ are unsubstituted, straight-chained octylene radicals; (ii) $R_3$ is an unsubstituted, straight-chained butylene radical; (iii) $R_2$ and $R_4$ are unsubstituted t-butyl radicals; (iv) $R_6$ is a pentylene radical; and (v) X is TEMPO; then, $L_2$ cannot be

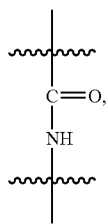

when the carbon of $L_2$ is attached to either $C_1$ or $C_5$ of the pentylene radical, $R_6$, and the nitrogen of the $L_2$ is connected to $C_1$ of the TEMPO. Moreover, if (i) $R_1$ and $R_5$ are straight-chained-butyl or straight-chained-hexyl radicals; (ii) $R_3$ is a straight-chained or branched saturated aliphatic radicals having from 2-20 carbon atoms; (iii) $R_2$ and $R_4$ are independently selected straight-chained or branched saturated aliphatic radicals having from 1-6 carbon atoms, straight-chained or branched aliphatic radicals having from 2-6 carbon atoms and at least one unsaturated carbon-carbon bond, straight-chained or branched aliphatic radicals having from 2-6 carbon atoms and at least one carbon-carbon triple bond, phenyl radicals, an ortho-fused bicyclic carbocyclic radical having 6-10 carbon atoms and at least one aromatic ring, or hydrogen; (iv) $R_6$ is a pentylene radical; (v) X is TEMPO and $L_2$ is

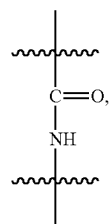

or X is rapamycin and $L_2$ is

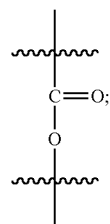

then, $R_1$ and $R_5$ cannot be substituted with epoxy groups.

In other embodiments, the invention can also include a polymer represented by a formula:

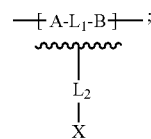

wherein A comprises

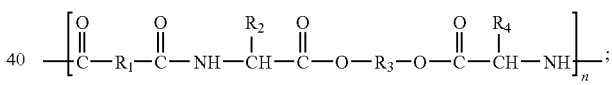

and B comprises

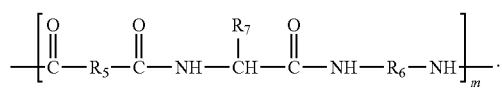

The groups $R_1$ and $R_5$ are optional and can be independently selected from substituted, unsubstituted, hetero-, straight-chained, branched, cyclic, saturated and unsaturated aliphatic radicals; and substituted, unsubstituted, and hetero-aromatic radicals. The group $R_3$ can be selected from substituted, unsubstituted, hetero-, straight-chained, branched, cyclic, saturated and unsaturated aliphatic radicals; and substituted, unsubstituted, and hetero-aromatic radicals. The groups $R_2$, $R_4$, and $R_7$ can be independently selected from hydrogen; substituted, unsubstituted, hetero-, straight-chained, branched, cyclic, saturated and unsaturated aliphatic radicals; and substituted, unsubstituted, and hetero-aromatic radicals. The group $R_6$ can be selected from substituted, unsubstituted, hetero-, straight-chained and branched aliphatic radicals. The group $L_1$ can be an optional linkage connecting A to B, and the group X can be optionally an agent. The group $L_2$ can optionally be a linkage connecting X to the polymer, and n and m are integers not equal to 0.

In other embodiments, the invention can also include a polymer represented by a formula:

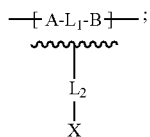

wherein A comprises

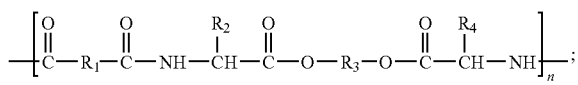

and B comprises

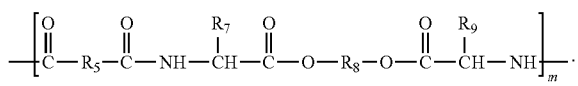

The groups $R_1$ and $R_5$ are optional and can be independently selected from substituted, unsubstituted, hetero-, straight-chained, branched, cyclic, saturated and unsaturated aliphatic radicals; and substituted, unsubstituted, and hetero-aromatic radicals. The group $R_3$ can be selected from substituted, unsubstituted, hetero-, straight-chained, branched, cyclic, saturated and unsaturated aliphatic radicals; and substituted, unsubstituted, and hetero-aromatic radicals. The groups $R_2$, $R_4$, $R_7$ and $R_9$ can be independently selected from hydrogen; substituted, unsubstituted, hetero-, straight-chained, branched, cyclic, saturated and unsaturated aliphatic radicals; and substituted, unsubstituted, and hetero-aromatic radicals. The group $R_8$ can be selected from substituted, unsubstituted, hetero-, straight-chained and branched aliphatic radicals. The group $L_1$ can be an optional linkage connecting A to B, and the group X can be optionally an agent. The group $L_2$ can optionally be a linkage connecting X to the polymer, and n and m are integers not equal to 0.

In other embodiments, the invention also provides poly (ester amide) coatings and coated medical articles that include an agent with properties that may be biobeneficial, bioactive, diagnostic or have a combination of these characteristics. In some embodiments, the medical article may include a stent that provides for local delivery of an agent.

DETAILED DESCRIPTION

Figure 1:
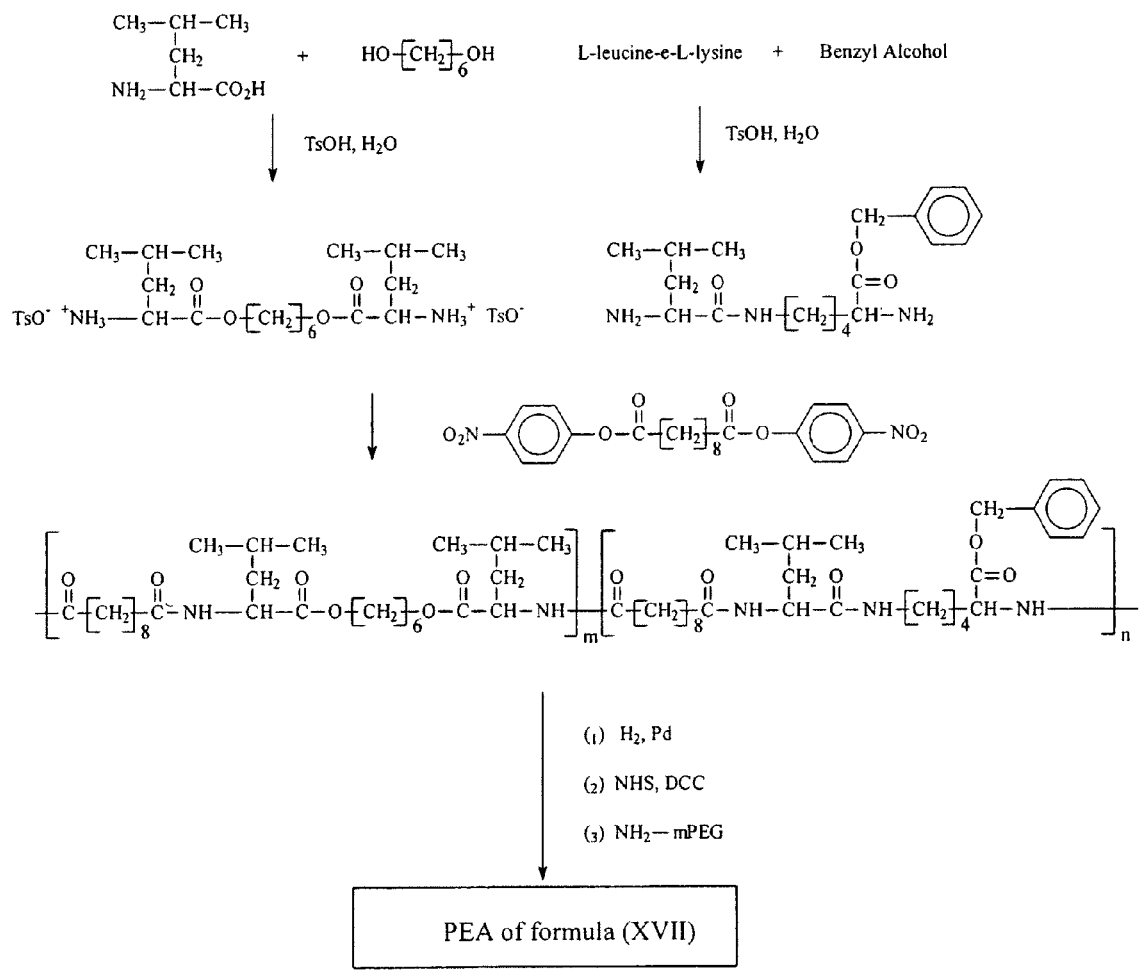
FIG. 1 illustrates a proposed reaction mechanism for the preparation of the poly(ester amide) (PEA) of formula (XVII) according to one embodiment of the present invention.

As discussed in more detail below, embodiments of the present invention generally encompass compositions including poly(ester amides) and agents such as therapeutic, prophylactic, diagnostic or other agents, for use with medical articles and methods for fabricating the compositions. The compositions can be a polymeric product of a reaction between a polyol, a polycarboxylic acid, an amino acid and, optionally, an agent. The medical articles comprise any medical device, which can be an implantable medical device such as a stent. In some embodiments, the compositions can be used as a coating on the implantable substrate. In other embodiments, a medical device such as a stent is made in whole or in part from the composition.

An "agent" can be a moiety that may be bioactive, biobeneficial, diagnostic or have a combination of these characteristics. A "moiety" can be a functional group composed of at least 2 atoms, a bonded residue in a macromolecule, an individual unit in a copolymer or an entire polymeric block. A "bioactive agent" is a moiety that can be linked to a polymer and provides a therapeutic effect, a prophylactic effect, both a therapeutic and a prophylactic effect, or other biologically active effect. A "bioactive agent" can also be combined, mixed or blended with a polymer. The bioactive agents of the present invention may remain linked to a portion of the polymer or be released from the polymer. A "biobeneficial agent" is an agent linked to a polymer that provides a biological benefit within a mammal without necessarily being released from the polymer. A "biobeneficial agent" can also be combined, mixed or blended with a polymer.

It is to be appreciated that any medical articles that can be improved through the teachings described herein are within the scope of the present invention. Examples of medical devices include, but are not limited to, stent-grafts, artificial heart valves, cerebrospinal fluid shunts, pacemaker electrodes, guidewires, ventricular assist devices, cardiopulmonary bypass circuits, blood oxygenators, coronary shunts (AXIUS™, Guidant Corp.) and endocardial leads (FINE-LINE® and ENDOTAK®, Guidant Corp.).

The medical devices can be comprised of a metal or an alloy, including, but not limited to, ELASTINITE® (Guidant Corp.), NITINOL® (Nitinol Devices and Components), stainless steel, tantalum, tantalum-based alloys, nickel-titanium alloy, platinum, platinum-based alloys such as, for example, platinum-iridium alloys, iridium, gold, magnesium, titanium, titanium-based alloys, zirconium-based alloys, alloys comprising cobalt and chromium (ELGILOY™, Elgiloy Specialty Metals, Inc.; MP35N and MP20N, SPS Technologies) or combinations thereof. The tradenames "MP35N" and "MP20N" describe alloys of cobalt, nickel, chromium and molybdenum. The MP35N consists of 35% cobalt, 35% nickel, 20% chromium, and 10% molybdenum. The MP20N consists of 50% cobalt, 20% nickel, 20% chromium, and 10% molybdenum. Medical devices with structural components that are comprised of bioabsorbable polymers or biostable polymers are also included within the scope of the present invention.

Preparing a Polymer

In one embodiment, a polymer used in preparing the composition is a PEA, which due to the labile nature of the ester groups, makes the PEA structure biodegradable. The PEA comprises at least one amide group and at least one ester group and, as a result, can have a wide variety of molecular configurations. Such a polymer can exhibit, for example, sufficient mechanical strength for stent coating applications and an ability to be broken down, absorbed, resorbed and eliminated by a mammal. For the purposes of the present invention, a polymer or coating is "biodegradable" when it is capable of being completely or substantially degraded or eroded when exposed to either an in vivo environment or an in vitro environment having physical, chemical, or biological characteristics substantially similar to those of the in vivo environment within a mammal. A polymer or coating is capable of being degraded or eroded when it can be gradually broken-down, resorbed, absorbed and/or eliminated by, for example, hydrolysis, enzymolysis, metabolic processes, bulk or surface erosion, and the like within a mammal. It should be appreciated that traces or residue of polymer may remain on the device following biodegradation. The terms "bioabsorbable" and "biodegradable" are used interchangeably in this application.

The polymers used in the present invention may be biodegradable and may include, but are not limited to, condensation copolymers. It should be appreciated, however, that if less than 100% of a biodegradable polymer is PEA, polymers other than PEA can compose the balance of composition. In addition, these other polymers can also be blended or cross-linked with the PEA using, for example, an isocyanate or a diisocyanate. If these other polymers are also biodegradable, the amount incorporated should be limited by their effect on a required performance parameter of a product formed from the biodegradable polymer. Such performance parameters may include, for example, the mechanical strength of a coating or the rate of biodegradation and elimination of a coating from a mammal. If the other polymers are non-biodegradable, the polymer fragments produced during biodegradation should have molecular weights of a size that ensures elimination of the fragments from a mammal. In some embodiments, the molecular weight of the polymer fragments should be at or below about 40,000 Daltons, or any range therein. In other embodiments, the molecular weight of the fragments range from about 300 Daltons to about 40,000 Daltons, from about 8,000 Daltons to about 30,000 Daltons, from about 10,000 Daltons to about 20,000 Daltons, or any range therein.

Examples of polymers that can be combined with the PEA include, but are not limited to, polyacrylates such as poly (butyl methacrylate), poly(ethyl methacrylate), and poly (ethyl methacrylate-co-butyl methacrylate); fluorinated polymers or copolymers such as poly(vinylidene fluoride) and poly(vinylidene fluoride-co-hexafluoro propene); poly(N-vinyl pyrrolidone); poly(hydroxyvalerate); poly(L-lactic acid); polycaprolactone; poly(lactide-co-glycolide); poly(hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly(trimethylene carbonate); poly(iminocarbonate); co-poly(ether-esters); polyalkylene oxalates; polyphosphazenes; biomolecules such as fibrin, fibrinogen, cellulose, starch, collagen and hyaluronic acid; polyurethanes; silicones; polyesters; polyolefins; polyisobutylene and ethylene-alphaolefin copolymers; vinyl halide polymers and copolymers such as polyvinyl chloride; polyvinyl ethers such as polyvinyl methyl ether; polyvinylidene chloride; polyacrylonitrile; polyvinyl ketones; polyvinyl aromatics such as polystyrene; polyvinyl esters such as polyvinyl acetate; copolymers of vinyl monomers with each other and olefins such as poly(ethylene-co-vinyl alcohol) (EVAL), ethylene-methyl methacrylate copolymers, acrylonitrile-styrene copolymers, ABS resins, and ethylene-vinyl acetate copolymers; polyamides such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; and carboxymethyl cellulose.

In some embodiments, the composition includes a polymer and an agent. In one embodiment, the composition can be a reaction product of a polyol, a polycarboxylic acid, an amino acid and, optionally, an agent.

The polyols used in the present invention may be organic compounds having two or more hydroxyl groups. In some embodiments, the polyols include, but are not limited to, cyclohexanedimethanol, glycerol, trimethylolpropane, pentaerythritol and compounds represented by a formula (I):

wherein R can be a substituted, unsubstituted, hetero-, straight-chained, branched, cyclic, saturated or unsaturated aliphatic radical; or a substituted, unsubstituted, or hetero-aromatic radical; and n is an integer. In some embodiments, the polyols are diols. Examples of diols that can be used include ethylene glycol, 1,2-propanediol, 1,3-propanediol, 1,4-butanediol, 1,5-pentanediol, 1,6-hexanediol, 1,7-heptanediol, 1,8-octanediol, 1,9-nonanediol, 1,10-decanediol, 1,11-undecanediol, 1,12-dodecanediol, dihydroxyacetone, and cyclohexanedimethanols such as, for example, 1,4-cis-cyclohexanedimethanol. In other embodiments, R can be a substituted or unsubstituted poly(alkylene glycols), which include, but are not limited to, poly(ethylene glycol) (PEG), methoxy poly(ethylene glycol) (mPEG), poly(ethylene oxide), poly(propylene glycol) (PPG), poly(tetramethylene glycol), poly(ethylene oxide-co-propylene oxide), or copolymers and combinations thereof. In one embodiment, the poly (alkylene glycol) is PEG. In another embodiment, the poly (alkylene glycol) is a PEG derivative such as mPEG. In another embodiment, R can be a co-polymer of PEG or a copolymer of a PEG derivative such as mPEG. The PEGs in all embodiments of the present invention can have molecular weights ranging from about 100 Daltons to about 4000 Daltons, from about 200 Daltons to about 2000 Daltons, from about 300 Daltons to about 1000 Daltons, from about 400 Daltons to about 900 Daltons, from about 500 Daltons to about 800 Daltons, or any range therein. It is to be appreciated that one skilled in the art should recognize that some of the groups, subgroups, and individual polyols may not be used in some embodiments of the present invention.

With respect to the chemical notation used herein, each of the functional groups, R, can be independently selected from substituted, unsubstituted, hetero-, straight-chained, branched, cyclic, saturated or unsaturated aliphatic radical; or a substituted, unsubstituted, or hetero-aromatic radicals. For example, an R group can be selected from H; aliphatic hydrocarbon groups such as, for example, alkyl, alkenyl, and alkynyl groups; aromatic groups such as, for example, aryl, aralkyl, aralkenyl, and aralkynyl groups; and, various other groups as defined below. In some embodiments of the present invention, the aliphatic radicals have from about 1 to about 50 carbon atoms, from about 2 to about 40 carbon atoms, from about 3 to about 30 carbon atoms, from about 4 to about 20 carbon atoms, from about 5 to about 15 carbon atoms, from about 6 to about 10 carbon atoms, and any range therein. In some embodiments, the aromatic radicals have from about 6 to about 180 carbon atoms, from about 12 to about 150 carbon atoms, from about 18 to about 120 carbon atoms, from about 24 to about 90 carbon atoms, from about 30 to about 60 carbon atoms, and any range therein.

The term "alkyl" refers to a straight-chained or branched hydrocarbon chain. Examples of alkyl groups include lower alkyl groups such as, for example, methyl, ethyl, n-propyl, iso-propyl, n-butyl, iso-butyl, t-butyl or iso-hexyl; upper alkyl groups such as for example, n-heptyl, n-octyl, iso-octyl, nonyl, decyl, and the like; lower alkylene such as, for example, ethylene, propylene, propylyne, butylenes, butadiene, pentene, n-hexene and iso-hexene; and upper alkylene such as, for example, n-heptene, n-octene, iso-octene, nonene, decene, and the like. Persons of ordinary skill in the art are familiar with numerous straight-chained and branched alkyl groups, which are within the scope of the present invention. In addition, such alkyl groups may also contain various substituents in which one or more hydrogen atoms is replaced by a functional group or an in-chain functional group. The phrase "straight-chained or branched" includes any substituted or unsubstituted acyclic carbon-containing compounds including, but not limited to, alkanes, alkenes and alkynes.

The term "alkenyl" refers to a straight-chained or branched hydrocarbon chain where at least one of the carbon-carbon linkages is a carbon-carbon double bond. The term "alkynyl" refers to a straight-chained or branched hydrocarbon chain where at least one of the carbon-carbon linkages is a carbon-carbon triple bond. The term "aryl" refers to a hydrocarbon ring bearing a system of conjugated double bonds often comprising at least six π (pi) electrons. Examples of aryl groups include, but are not limited to, phenyl, naphthyl, anysyl, toluoyl, xylenyl, and the like. The term "aralkyl" refers to an alkyl group substituted with at least one aryl group. The term "aralkenyl" refers to an alkenyl group substituted with at least one aryl group.

A radical is "straight-chained" when it has less than 0.1 mole percent of sidechains having 1 or more carbon atoms. In some embodiments, a radical is straight-chained if it has less than 0.01 mole percent of such sidechains. In other embodiments, a radical is straight-chained if it has less than 0.001 mole percent of such sidechains. A radical is "branched" when it has more than 0.1 mole percent of sidechains having 1 or more carbon atoms. In some embodiments, a radical is branched when it has more than 0.01 mole percent of such sidechains. In other embodiments, a radical is branched when it has more than 0.001 mole percent of such sidechains. The terms "radical," "group," "functional group," and "substituent" can be used interchangeably in some contexts and can be used together to further describe a chemical structure. For example, the term "functional group" can refer to a chemical "group" or "radical," which is a chemical structure variable that is in-chain, pendant and/or terminal to the chemical structure. Such a functional group may be substituted. Examples of substituents in substituted radicals include, but are not limited to, hydroxyls, carboxyls, aminos, amidos, iminos and combinations thereof. Such a functional group can also, for example, contain a heteroatom. Examples of heteroatoms of the hetero-radicals include, but are not limited to, sulfur, phosphorous, oxygen, nitrogen and combinations thereof.

The polycarboxylic acids used in the present invention may be organic acids having two or more carboxyl groups. In some embodiments, the polycarboxylic acids include dicarboxylic acids and tricarboxylic acids and may be aliphatic or aromatic structures. In one embodiment, the polycarboxylic acids are represented by a formula (II):

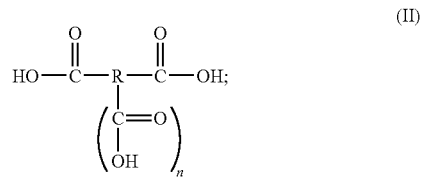

wherein R is optional and can be a substituted, unsubstituted, hetero-, straight-chained, branched, cyclic, saturated or unsaturated aliphatic radical; and a substituted or unsubstituted aromatic radical; and n is an integer. Examples of polycarboxylic acids include, but are not limited to, oxalic acid, malonic acid, succinic acid, glutaric acid, adipic acid, pimelic acid, suberic acid, sebacic acid, azelaic acid, terephthalic acid, citric acid, maleic acid, fumaric acid and combinations thereof. It is to be appreciated that one skilled in the art should recognize that some of the groups, subgroups, and individual polycarboxylic acids may not be used in some embodiments of the present invention.

In some embodiments, R is a methylene [—$(CH_2)_y$—] or phenylene group [—$C_6H_4$—], where y is an integer between 0 and 16. In other embodiments, R can be a substituted or unsubstituted poly(alkylene glycols), which include, but are not limited to, PEG, PEG derivatives such as mPEG, poly(ethylene oxide), PPG, poly(tetramethylene glycol), poly(ethylene oxide-co-propylene oxide), or copolymers and combinations thereof. In one embodiment, the poly(alkylene glycol) is PEG. In another embodiment, the poly(alkylene glycol) is a PEG derivative such as mPEG. In another embodiment, R can be a co-polymer of PEG or a copolymer of a PEG derivative such as mPEG. In other embodiments R can be aryl. In other, embodiments, R may not be substituted with an epoxy group. In other embodiments, R may not comprise a PEG.

The amino acids used in the present invention may be organic compounds comprising an amino group and a carboxyl group, and the amino group may be primary or secondary. Examples of amino acids include, but are not limited to, glycine, alanine, valine, leucine, isoleucine, methionine, phenylalanine, tyrosine, aspartic acid, glutamic acid, lysine, arginine, serine, threonine, cysteine, asparagine, proline, tryptophan, histidine and combinations thereof. In some embodiments, the amino acids are represented by a formula (III):

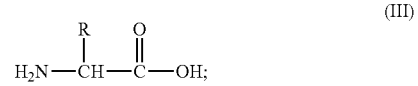

wherein R may be a hydrogen; a substituted, unsubstituted, hetero-, straight-chained, branched, cyclic, saturated or unsaturated aliphatic radical; or a substituted, unsubstituted, or hetero-aromatic radical. In some embodiments, R can be substituted, unsubstituted, or hetero-forms of methyl, iso-propyl, sec-butyl, iso-butyl, benzyl, or a combination thereof.

In embodiments where R is substituted, examples of substitutents include, but are not limited to, hydroxyl, carboxyl, amino, imino groups and combinations thereof. In embodiments where R is heteroaliphatic, examples of heteroatoms include, but are not limited to, sulfur, phosphorous, oxygen, nitrogen and combinations thereof. In other embodiments, R can comprise substituted or unsubstituted poly(alkylene glycols), which include, but are not limited to, PEG, PEG derivatives such as mPEG, poly(ethylene oxide), PPG, poly(tetramethylene glycol), poly(ethylene oxide-co-propylene oxide), or copolymers and combinations thereof. In one embodiment, the poly(alkylene glycol) is PEG. In another embodiment, the poly(alkylene glycol) may comprise a PEG derivative such as mPEG. In another embodiment, R can comprise a co-polymer of PEG or a copolymer of a PEG derivative such as mPEG.

In some embodiments, the amino acids may be limited to bifunctional amino acids. In some embodiments, the amino acids may be limited to trifunctional amino acids. In some embodiments, the amino acids may be limited to diamines. In some embodiments, the amino acids may be limited to triamines. In some embodiments, the amino acids may be limited to monocarboxylics. In some embodiments, the amino acids may be limited to dicarboxylics. In some embodiments, the amino acids may be limited to aliphatics. In some embodiments, the amino acids may be limited to aromatics. In some embodiments, the amino acids may be limited to amides. In some embodiments, the amino acids may not include lysine. It is to be appreciated that one skilled in the art should recognize that some of the groups, subgroups, and individual amino acids may not be used in some embodiments of the present invention.

Biobeneficial and Bioactive Agents

In some embodiments, the agents are linked to a polymer and can be biobeneficial, bioactive, diagnostic or have a combination of these characteristics. Biobeneficial agents are moieties that may be linked to the polymer and are capable of providing a biological benefit such as, for example, control of protein adsorption, without being released from the polymer. In some embodiments, the biobeneficial agents can be released or separate from the polymer. In other embodiments, the biobeneficial agents should have a reactive group that can be used to link the agent to the polymer. Examples of reactive groups include, but are not limited to, hydroxyl, carboxyl, and amino groups. In some embodiments, the molecular weight of the agent should be at or below about 40,000 Daltons, or any range therein, to ensure elimination of the agent from a mammal. In one embodiment, the molecular weight of the agent ranges from about 300 Daltons to about 40,000 Daltons, from about 8,000 Daltons to about 30,000 Daltons, from about 10,000 Daltons to about 20,000 Daltons, or any range therein. It is to be appreciated that one skilled in the art should recognize that some of the groups, subgroups, and individual biobeneficial agents may not be used in some embodiments of the present invention.

Examples of biobeneficial agents include, but are not limited to, poly(alkylene glycols), poly(N-vinyl pyrrolidone), poly(acrylamide methyl propane sulfonic acid), poly(styrene sulfonate), sulfonated dextran, polyphosphazenes, poly(orthoesters), poly(tyrosine carbonate), hyaluronic acid, heparin and any derivatives, analogs, homologues, congeners, salts, copolymers and combinations thereof.

Examples of heparin derivatives include, but are not limited to, earth metal salts of heparin such as, for example, sodium heparin, potassium heparin, lithium heparin, calcium heparin, magnesium heparin, and low molecular weight heparin. Other examples of heparin derivatives include, but are not limited to, heparin sulfate, heparinoids, heparin-based compounds and heparin derivatized with hydrophobic materials.

The poly(alkylene glycols) include, but are not limited to, PEG, mPEG, poly(ethylene oxide), PPG, poly(tetramethylene glycol), poly(ethylene oxide-co-propylene oxide) and any derivatives, analogs, homologues, congeners, salts, copolymers and combinations thereof. In one embodiment, the poly(alkylene glycol) is mPEG.

The copolymers that may be used as biobeneficial agents include, but are not limited to, any derivatives, analogs, homologues, congeners, salts, copolymers and combinations of the foregoing examples of biobeneficial agents. Examples of copolymers that may be used as biobeneficial agents in the present invention include, but are not limited to, copolymers of PEG and hyaluronic acid; copolymers of PEG and heparin; graft copolymers of poly(L-lysine) and PEG; and, any derivative, analog, congener, salt, or combination thereof, of the copolymers. In one embodiment, the copolymer that may be used as a biobeneficial agent is a copolymer of PEG and hyaluronic acid, or any derivative, analog, congener, salt, copolymer or combination thereof.

The bioactive agents can be any moiety capable of contributing to a therapeutic effect, a prophylactic effect, both a therapeutic and prophylactic effect, or other biologically active effect in a mammal. The agent can also have diagnostic properties. The bioactive agents include, but are not limited to, small molecules, nucleotides, oligonucleotides, polynucleotides, amino acids, oligopeptides, polypeptides, and proteins. In one example, the bioactive agent inhibits the activity of vascular smooth muscle cells. In another example, the bioactive agent controls migration or proliferation of smooth muscle cells to inhibit restenosis.

Bioactive agents include, but are not limited to, antiproliferatives, antineoplastics, antimitotics, anti-inflammatories, antiplatelets, anticoagulants, antifibrins, antithrombins, antibiotics, antiallergics, antioxidants, and any prodrugs, metabolites, analogs, homologues, congeners, derivatives, salts and combinations thereof. It is to be appreciated that one skilled in the art should recognize that some of the groups, subgroups, and individual bioactive agents may not be used in some embodiments of the present invention.

Antiproliferatives include, for example, actinomycin D, actinomycin IV, actinomycin $I_1$, actinomycin $X_1$, actinomycin $C_1$, and dactinomycin (COSMEGEN™, Merck & Co., Inc.). Antineoplastics or antimitotics include, for example, paclitaxel (TAXOL®, Bristol-Myers Squibb Co.), docetaxel (TAXOTERE®, Aventis S.A.), methotrexate, azathioprine, vincristine, vinblastine, fluorouracil, doxorubicin hydrochloride (ADRIAMYCIN®, Pfizer, Inc.) and mitomycin (MUTAMYCIN®, Bristol-Myers Squibb Co.), and any prodrugs, metabolites, analogs, homologues, congeners, derivatives, salts and combinations thereof. Antiplatelets, anticoagulants, antifibrin, and antithrombins include, for example, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors (ANGIOMAX®, Biogen, Inc.), and any prodrugs, metabolites, analogs, homologues, congeners, derivatives, salts and combinations thereof. Cytostatic or antiproliferative agents include, for example, angiopeptin, angiotensin converting enzyme inhibitors such as captopril (CAPOTEN® and CAPOZIDE®, Bristol-Myers Squibb Co.), cilazapril or lisinopril (PRINIVIL® and PRINZIDE®, Merck & Co., Inc.); calcium channel blockers such as nifedipine; colchicines; fibroblast growth factor (FGF) antagonists, fish oil (omega 3-fatty acid); histamine antagonists; lovastatin (MEVACOR®, Merck & Co., Inc.); monoclonal antibodies including, but not limited to, antibodies specific for Platelet-Derived Growth Factor (PDGF) receptors; nitroprusside; phosphodiesterase inhibitors; prostaglandin inhibitors; suramin; serotonin blockers; steroids; thioprotease inhibitors; PDGF antagonists including, but not limited to, triazolopyrimidine; and nitric oxide, and any prodrugs, metabolites, analogs, homologues, congeners, derivatives, salts and combinations thereof. Antiallergic agents include, but are not limited to, pemirolast potassium (ALAMAST®, Santen, Inc.), and any prodrugs, metabolites, analogs, homologues, congeners, derivatives, salts and combinations thereof.

Other bioactive agents useful in the present invention include, but are not limited to, free radical scavengers; nitric oxide donors; rapamycin; everolimus; tacrolimus; 40-O-(2-hydroxy)ethyl-rapamycin; 40-O-(3-hydroxy)propyl-rapamycin; 40-O-[2-(2-hydroxy)ethoxy]ethyl-rapamycin; tetrazole containing rapamycin analogs such as those described in U.S. Pat. No. 6,329,386; estradiol; clobetasol; idoxifen; tazarotene; alpha-interferon; host cells such as epithelial cells; genetically engineered epithelial cells; dexamethasone; and, any prodrugs, metabolites, analogs, homologues, congeners, derivatives, salts and combinations thereof.

Free radical scavengers include, but are not limited to, 2,2',6,6'-tetramethyl-1-piperinyloxy, free radical (TEMPO); 4-amino-2,2',6,6'-tetramethyl-1-piperinyloxy, free radical (4-amino-TEMPO); 4-hydroxy-2,2',6,6'-tetramethyl-piperidene-1-oxy, free radical (TEMPOL), 2,2',3,4,5,5'-hexamethyl-3-imidazolinium-1-yloxy methyl sulfate, free radical; 16-doxyl-stearic acid, free radical; superoxide dismutase mimic (SODm) and any analogs, homologues, congeners, derivatives, salts and combinations thereof. Nitric oxide donors include, but are not limited to, S-nitrosothiols, nitrites, N-oxo-N-nitrosamines, substrates of nitric oxide synthase, diazenium diolates such as spermine diazenium diolate and any analogs, homologues, congeners, derivatives, salts and combinations thereof.

It should be appreciated that the agents of the present invention can have both biobeneficial and bioactive properties, and that classification of an agent as a biobeneficial agent does not preclude the use of that agent as a bioactive agent. Likewise, classification of an agent as a bioactive agent does not preclude the use of that agent as a biobeneficial agent. It should also be appreciated that any of the foregoing agents can be mixed or blended with the PEAs such as in the form of a coated medical device. By way of example, a stent coated with the PEA embodiments of the invention can contain paclitaxel, docetaxel, rapamycin or everolimus.

PEA-Agent Combinations

The agents of the present invention can be connected to a PEA as a pendant group or as an in-chain group. It should be appreciated that the agent can be a polymeric agent, which can be attached as a pendant group or as an in-chain group.

1. The Agent as a Pendant Group

A polymer of the present invention can comprise a polymeric carrier having an A-moiety (A), a B-moiety (B), and an optional linkage ($L_1$) connecting A to B. The remainder of the polymer comprises an agent (X), and a linkage ($L_2$) connecting X to the polymer. This PEA-agent combination can be generally represented by a formula (IV):

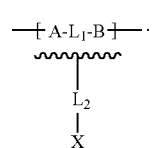

(IV)

In formula (IV), both A and B can be independently selected and comprise any combination of monomers such that the polymer has at least one ester group and one amide group. In some embodiments, the ester and amide are adjacent. Optionally, A and B can be connected by $L_1$, which can be a substituted, unsubstituted, hetero-, straight-chained, branched, cyclic, saturated or unsaturated aliphatic radical; and a substituted or unsubstituted aromatic radical. In some embodiments, $L_1$ can comprise from about 0 to about 50 carbon atoms, from about 2 to about 40 carbon atoms, from about 3 to about 30 carbon atoms, from about 4 to about 20 carbon atoms, from about 5 to about 10 carbon atoms, and any range therein. In other embodiments, the $L_1$ can alternately comprise a non-carbon species such as, for example, a disulfide. In other embodiments, $L_1$ can comprise substituted or unsubstituted poly(alkylene glycols), which include, but are not limited to, PEG, PEG derivatives such as mPEG, poly (ethylene oxide), PPG, poly(tetramethylene glycol), poly (ethylene oxide-co-propylene oxide), or copolymers and combinations thereof. In one embodiment, the poly(alkylene glycol) is PEG. In another embodiment, the poly(alkylene glycol) may comprise a PEG derivative such as mPEG. In another embodiment, $L_1$ can comprise a co-polymer of PEG or a copolymer of a PEG derivative such as mPEG.

In some embodiments, X can also be optional and can be connected to the polymer by $L_2$, which can be any interunit linkage such as, for example, an ester, an anhydride, an acetal, an amide, a urethane, a urea, a glycoside, a disulfide, and a siloxane linkage. It is to be appreciated that one skilled in the art should recognize that some of these linkages may not be used in some embodiments of the present invention.

The selection of $L_2$ allows for control of the relative strength or stability of the bond between X and the polymeric carrier as compared to the strength or stability of the bonds within the polymeric carrier. Control over this relative strength or stability allows for release of bioactive agents that are substantially free of attached molecules from the polymeric carrier. The agent, X, can be biobeneficial, bioactive, diagnostic or a have a combination of these characteristics, and is discussed in detail above.

In some embodiments, A can be represented by a formula (V):

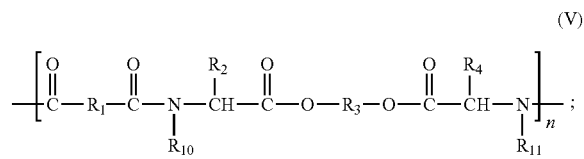

and in other embodiments, B can be represented by any of formulas (VI)-(VIII);

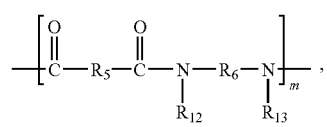

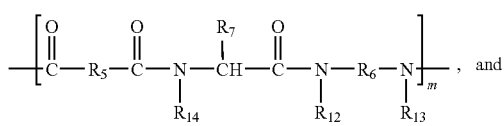

-continued

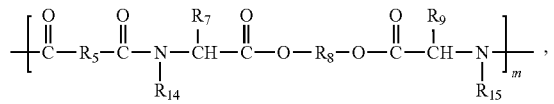

(VIII)

where $R_1$ and $R_5$ can be optional and can also be independently selected from a substituted, unsubstituted, hetero-, straight-chained, branched, cyclic, saturated or unsaturated aliphatic radical; or a substituted, unsubstituted, or heteroaromatic radical; $R_3$ and $R_8$ can be independently selected from a substituted, unsubstituted, hetero-, straight-chained, branched, cyclic, saturated or unsaturated aliphatic radical; or a substituted, unsubstituted, or hetero-aromatic radical; $R_2$ and $R_4$ can be independently selected from a hydrogen; a substituted, unsubstituted, hetero-, straight-chained, branched, cyclic, saturated or unsaturated aliphatic radical; or a substituted, unsubstituted, or hetero-aromatic radical; $R_6$ can be selected from a substituted, unsubstituted, hetero-, straight-chained or branched aliphatic radical; $R_7$ and $R_9$ can be independently selected from a hydrogen; a substituted, unsubstituted, hetero-, straight-chained, branched, cyclic, saturated or unsaturated aliphatic radical; and a substituted or unsubstituted aromatic radical; $R_{10}$ through $R_{15}$ can be independently selected from a hydrogen; a substituted, unsubstituted, hetero-, straight-chained, branched, cyclic, saturated or unsaturated aliphatic radical; or a substituted, unsubstituted, or hetero-aromatic radical; m can range from about 4 to about 1400, from about 10 to about 800, from about 20 to about 400, or any range therein; n can range from about 3 to about 1400, from about 10 to about 800, from about 20 to about 400, or any range therein; and the sum of m and n and can range from about 30 to about 1600, from about 50 to about 1200, from about 75 to about 900, from about 100 to about 600, or any range therein. In some embodiments, groups $R_{10}$ through $R_{15}$ are limited to hydrogen. In other embodiments, $R_1$ is not equal to $R_5$.

The polymers of the present invention can generally be prepared in the following manner: a polyester-type adduct is prepared by combining an amino acid with a diol. In some embodiments, the amino acid is a bi-functional amino acid. The polyester adduct can be combined with a multi-functional amino acid, a diacid or derivative of a diacid, and an agent. In embodiments where a peptide-type adduct is desired, two amino acids can be independently selected and combined such as, for example, where one amino acid is bi-functional and the other is multi-functional. An example of a multi-functional amino acid is a tri-functional amino acid. Examples of tri-functional amino acids include, but are not limited to, lysine, tyrosine, arginine, or glutamic acid. Examples of diacids include, but are not limited to, the dicarboxylic acids listed above. Examples of derivatives of diacids include, but are not limited to, diacid chloride, a dianhydride, or a di-p-nitrophenyl ester. In the event that a dicarboxylic acid is used, the reaction may be carried out in the presence of 1-ethyl-3(3-dimethylaminopropyl)carbodiimide (EDC) or 1,3-dicyclohexylcarbodiimide (DCC) in a solvent such as dimethylformamide (DMF) or tetrahydrofuran (THF). If a diacid chloride or di-p-nitrophenyl ester is used, an excess of pyridine or triethylamine should be present. Examples of other solvents that may be used include, but are not limited to, dimethylacetamide (DMAC), dimethylsulfoxide (DMSO), acetone, and dioxane.

The reaction conditions should be anhydrous and favor esterification of the amino acid's carboxyl group. In some embodiments, the reaction solvents include toluene and benzene and should be distilled to remove water. The reaction can be catalyzed by a strong acid or base such as, for example, p-toluenesulfonic acid (TsOH). In some embodiments, the temperature of the reaction ranges from about 25° C. to about 150° C., from about 35° C. to about 100° C., from about 50° C. to about 80° C., or any range therein. In some embodiments, the reaction times range from about 1 hour to about 24 hours, from about 6 hours to about 18 hours, from about 10 hours to about 14 hours, or any range therein. Any agent described above can be used.

Trifunctional amino acids can be incorporated into the polymer by protecting the third functionality with a protecting group that is later removed. Examples of protecting groups are benzyl esters for the lysine carboxyl or t-butoxycarbonyl for amino groups such as, for example, the amino group in glutamic acid. In some embodiments, the amino acid that is selected to link with the agent is not lysine.

The benzyl ester protecting group may be removed from the lysine carboxyl by hydrogenolysis with hydrogen gas over a catalyst such as, for example, palladium or platinum on carbon. Examples of suitable solvents include, but are not limited to, ethanol, methanol, isopropanol, and THF. In some embodiments, the reaction may be conducted under about 1 atm of hydrogen for about 6 hours to about 24 hours, for about 8 hours to about 16 hours, for about 10 hours to about 14 hours, or any range therein. After removal of the protecting group, an agent comprising an amino, a hydroxyl, a thiol, or a combination thereof is connected to the carboxyl group. Coupling agents used to connect the agent include, but are not limited to, EDC and DCC. Thionyl chloride or phosphorous pentachloride may be used in a less selective process of preparing the acid chloride derivative.

An amine functional compound such as, for example, 4-amino-TEMPO, may be connected to a polymer containing free carboxyls such as, for example, the lysine-derived carboxyls, by first activating the carboxyls and coupling the amine in a solvent under agitation. The carboxyls may be activated with, for example, N-hydroxysuccinimide (NHS) and DCC in a solvent such as, for example, THF or chloroform, which produces N-hydroxysuccinimidyl ester. Examples of the solvent that may be used to couple the amine to the carboxyls include, but are not limited to, THF and DMF. In some embodiments, the reaction occurs at a temperature ranging from about 5° C. to about 50° C., from about 15° C. to about 35° C., from about 20° C. to about 30° C., or any range therein. In some embodiments, the reaction time ranges from about 0.5 hours to about 24 hours, from about 1 hour to about 18 hours, from about 4 hours to about 16 hours, from about 6 hours to about 12 hours, or any range therein.

In one embodiment, a family of PEAs can be prepared by reacting a diol, a diacid, two independently selected amino acids, and an agent. The resulting product is PEA represented by a formula (IX):

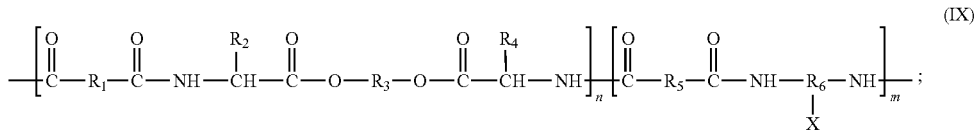

where the groups $R_1$ and $R_5$ can be optional and can also be independently selected substituted, unsubstituted, hetero-, straight-chained, branched, cyclic, saturated or unsaturated aliphatic radicals; or substituted or unsubstituted aromatic radicals. The group $R_3$ can be a substituted, unsubstituted, hetero-, straight-chained, branched, cyclic, saturated or unsaturated aliphatic radical; or a substituted, unsubstituted, or hetero-aromatic radical. The groups $R_2$ and $R_4$ can be independently selected hydrogens; substituted, unsubstituted, hetero-, straight-chained, branched, cyclic, saturated or unsaturated aliphatic radicals; or substituted or unsubstituted aromatic radicals. The group $R_6$ can be a substituted, unsubstituted, hetero-, straight-chained or branched aliphatic radical. The group X can be an agent; and n and m are integers not equal to 0.

Note, however, that in some embodiments, the polymers of the present invention do not comprise the following combination of the A-moiety, B-moiety, $L_2$, and X as represented by a formula (X):

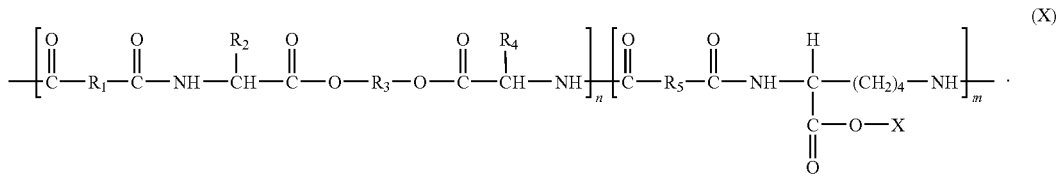

In formula (X), the groups $R_1$, $R_3$ and $R_5$ are independently selected, straight-chained or branched, saturated, aliphatic radicals having from 2-20 carbon atoms. The groups $R_2$ and $R_4$ are independently selected, straight-chained or branched, saturated, aliphatic radicals having from 1-6 carbon atoms; straight-chained or branched, aliphatic radicals having from 2-6 carbon atoms and at least one unsaturated carbon-carbon bond; straight-chained or branched, aliphatic radicals having from 2-6 carbon atoms and at least one carbon-carbon triple bond; phenyl radicals; an ortho-fused bicyclic carbocyclic radical having 6-10 carbon atoms and at least one aromatic ring; or hydrogen. The group X is a straight-chained or branched, saturated, aliphatic radical having from 1-6 carbon atoms; a phenyl radical; an ortho-fused bicyclic carbocyclic radical having 6-10 carbon atoms and at least one aromatic ring; or hydrogen. The subscripts m and n are integers not equal to 0.

In some embodiments of the present invention, diacids comprising epoxy groups may not be used to produce the PEAs. In other embodiments, diacids comprising epoxy groups may not be used to produce the PEAs where the amino acid chosen to link with X is lysine, and X is 4-amino-TEMPO or rapamycin. In other embodiments, $R_1$ and $R_5$ may not be substituted with epoxy groups where $R_1$ and $R_5$ are straight-chained-butylene or straight-chained-hexylene radicals. In other embodiments, $R_1$ and $R_5$ may not be substituted with epoxy groups where $R_1$ and $R_5$ are straight-chained-butylene or straight-chained-hexylene radicals, and X is TEMPO or rapamycin. In other embodiments, $R_1$ and $R_5$ may not be substituted with epoxy groups where $R_1$ and $R_5$ are straight-chained-butylene or straight-chained-hexylerie radicals, when X is 4-amino-TEMPO or rapamycin, and $L_2$ is the following ester linkage prior to connecting X to $L_2$:

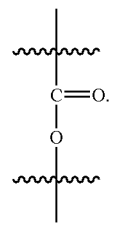 [SMILES: *OC(*)=O]

In other embodiments, $R_1$ and $R_5$ may not be substituted with epoxy groups where $R_1$ and $R_5$ are straight-chained-butylene or straight-chained-hexylene radicals, and (i) X is TEMPO and $L_2$ is

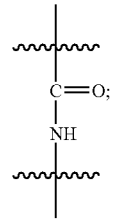

or, (ii) X is rapamycin and $L_2$ is

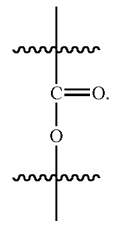 [SMILES: *OC(*)=O]

In other embodiments, a PEA may not be produced from a polycarboxylic acid that is 2,3-epoxysuccinic acid, 3,4-epoxyadipic acid or a diepoxyadipic acid, where the amino acid chosen to link with X is lysine, and X is 4-amino-TEMPO or rapamycin. In other embodiments, $R_1$ is not the same as $R_5$.

In formula (X), $L_2$ is an ester, which may be undesirable in some embodiments. As illustrated and described below, the careful selection of $L_2$ can help alleviate regulatory issues that may arise from the creation of derivatives of X during biodegradation of the polymers. Examples of $L_2$ include, but are not limited to, amides, esters, anhydrides, ketals, acetals, orthoesters and all-aromatic carbonates. In some embodiments, $L_2$ can be an ester, an anhydride, a ketal, an acetal, an orthoester, or an all-aromatic carbonates. In some embodiments, $L_2$ can be an anhydride, a ketal, an acetal, an orthoester or an all-aromatic carbonate. In some embodiments, $L_2$ can be a ketal, an acetal, an orthoester or an all-aromatic carbonate.

In some embodiments, $L_2$ can be an acetal, an orthoester or an all-aromatic carbonate. In some embodiments, $L_2$ can be an orthoester or an all-aromatic carbonate. In some embodiments, $L_2$ can be an all-aromatic carbonate, which includes linkages comprising moieties represented by formula (XI):

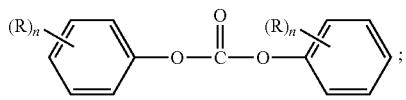

(XI)

wherein R is optional and can be independently selected from, for example, a substituted, unsubstituted, hetero-, straight-chained, branched, cyclic, saturated and unsaturated aliphatic radicals; substituted and unsubstituted aromatic radicals; and combinations thereof. The subscript n is an integer not equal to 0.

In some embodiments, the PEA is represented by a formula (XII):

wherein n, m, and r are integers not equal to 0. In formula (XII), the diol is hexane-1,6-diol, the diacid is sebacic acid, one amino acid is leucine, the other amino acid is lysine, and the agent is mPEG. The mPEG is connected to the B-moiety through an amide linkage, which is a stable linkage relative to the stability of the remainder of the polymer.

Formula (XIII) represents a polymer with an amide linkage. Note, however, that in some embodiments, a PEA represented by formula (XIII) is not within the scope of the present invention:

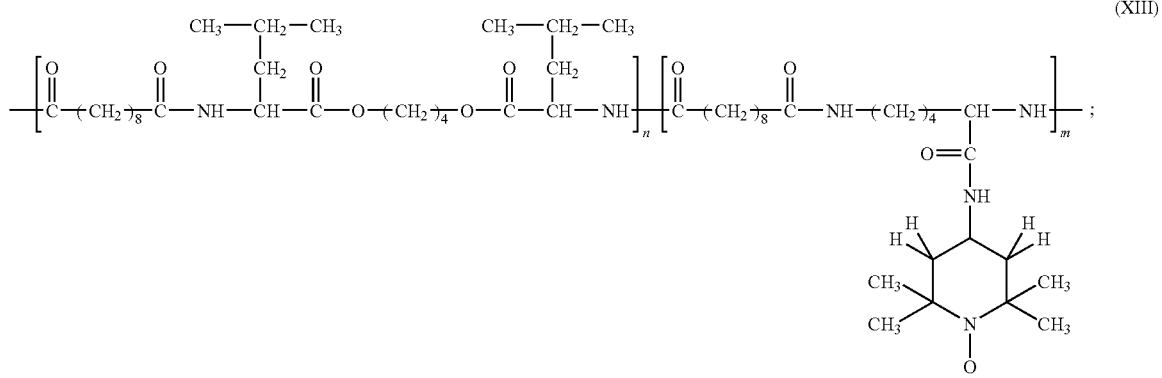

(XIII)

wherein n and m are integers not equal to 0. In formula (XIII), the diol is butane-1,6-diol, the diacid is sebacic acid, one amino acid is leucine, the other amino acid is lysine, and the agent is TEMPO. The TEMPO is connected to the B-moiety through an amide linkage, which may remain intact during biodegradation of the polymer resulting in attachment of additional molecules to the TEMPO that were derived from degradation of the polymer at the ester linkages. As a result, such a released agent would be a derivative of TEMPO rather than TEMPO and could cause regulatory concerns.

In some embodiments, the PEA is represented by a formula (XIV):

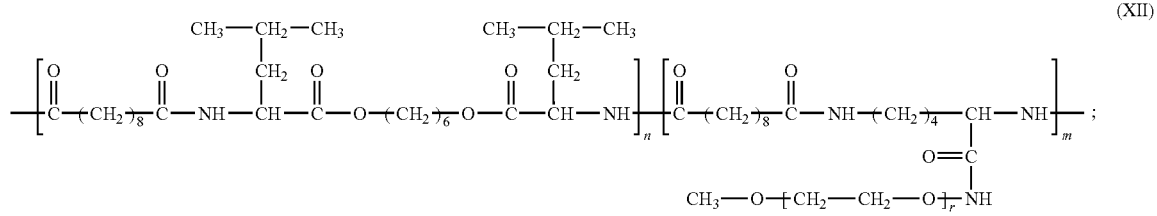

(XII)

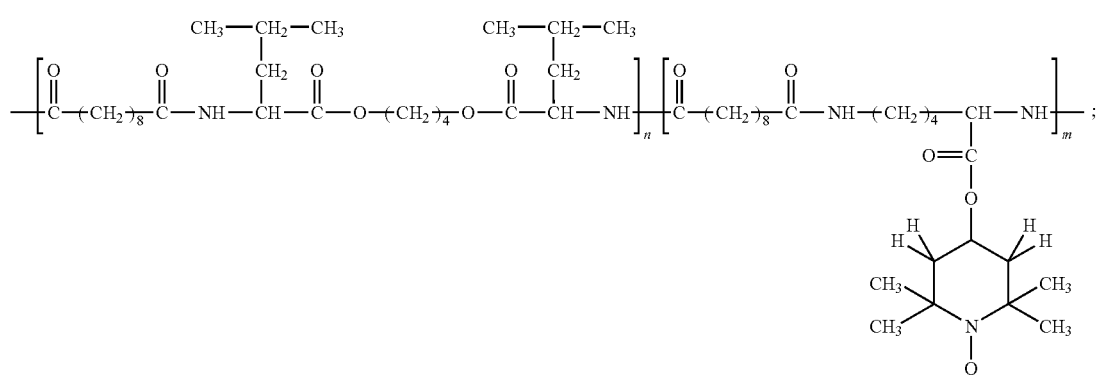

(XIV)

wherein n and m are integers not equal to 0. In formula (XIV), the diol is butane-1,6-diol, the diacid is sebacic acid, one amino acid is leucine, the other amino acid is lysine, and the agent is TEMPO. The TEMPO is connected to the B-moiety through an ester linkage, which is more labile than an amide linkage and allows for release of the agent from the polymer. The cleavage of the $L_2$ ester competes with the cleavage of the PEA esters and may result in attachment of additional molecules to the TEMPO that were derived from degradation of the polymer at ester linkages.

In some embodiments, the PEA is represented by a formula (XV):

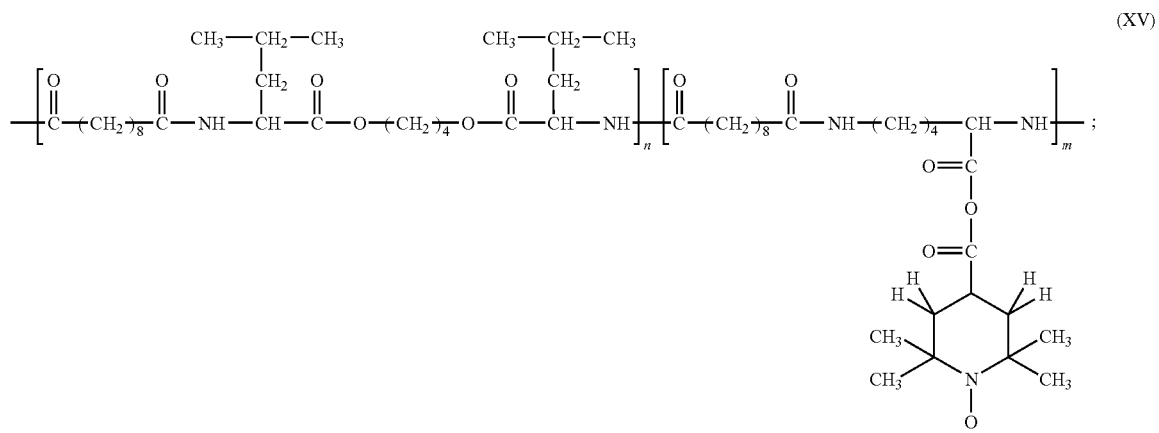

(XV)

wherein n and m are integers not equal to 0. In formula (XV), the diol is butane-1,6-diol, the diacid is sebacic acid, one amino acid is leucine, the other amino acid is lysine, and the agent is TEMPO. The TEMPO is connected to the B-moiety through an anhydride linkage, which is more labile than an ester linkage and, thus, may allow for release of the agent without attachment of additional molecules derived from biodegradation of the polymer at ester linkages.

In another embodiment, a family of PEAs comprising a dipeptide fragment can be prepared by reacting a diol, a diacid, two different amino acids, and an agent. The resulting product is a PEA represented by a formula (XVI):

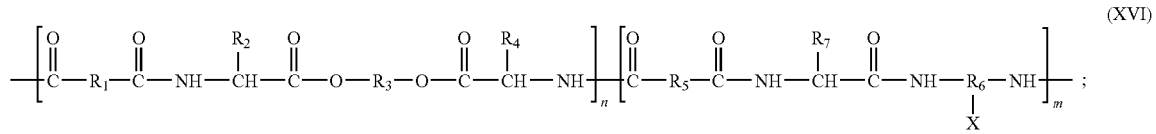

(XVI)

wherein where $R_1$ and $R_5$ can be optional and can also be independently selected from a substituted, unsubstituted, hetero-, straight-chained, branched, cyclic, saturated or unsaturated aliphatic radical; or a substituted, unsubstituted, or hetero-aromatic radical; $R_3$ can be independently selected from a substituted, unsubstituted, hetero-, straight-chained, branched, cyclic, saturated or unsaturated aliphatic radical; or a substituted, unsubstituted, or hetero-aromatic radical; $R_2$, $R_4$ and $R_7$ can be independently selected from a hydrogen; a substituted, unsubstituted, hetero-, straight-chained, branched, cyclic, saturated or unsaturated aliphatic radical; or a substituted, unsubstituted, or hetero-aromatic radical; $R_6$ can be selected from a substituted, unsubstituted, hetero-, straight-chained or branched aliphatic radical; X can be an agent; m can range from about 4 to about 1400; n can range from about 3 to about 1400; and the sum of m and n and can range from about 30 to about 1600.

In some embodiments, the PEA is represented by a formula (XVII):

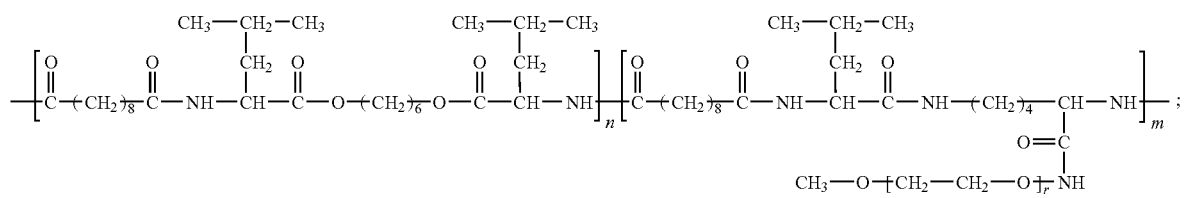

wherein n, m, and r are integers not equal to 0. In formula (XVII), the diol is hexane-1,6-diol, the diacid is sebacic acid, one amino acid is leucine, the other amino acid is lysine, X is mPEG and $L_2$ is an amide, which is stable relative to the stability of the remainder of the polymer.

In some embodiments, the PEA is represented by a formula (XVIII):

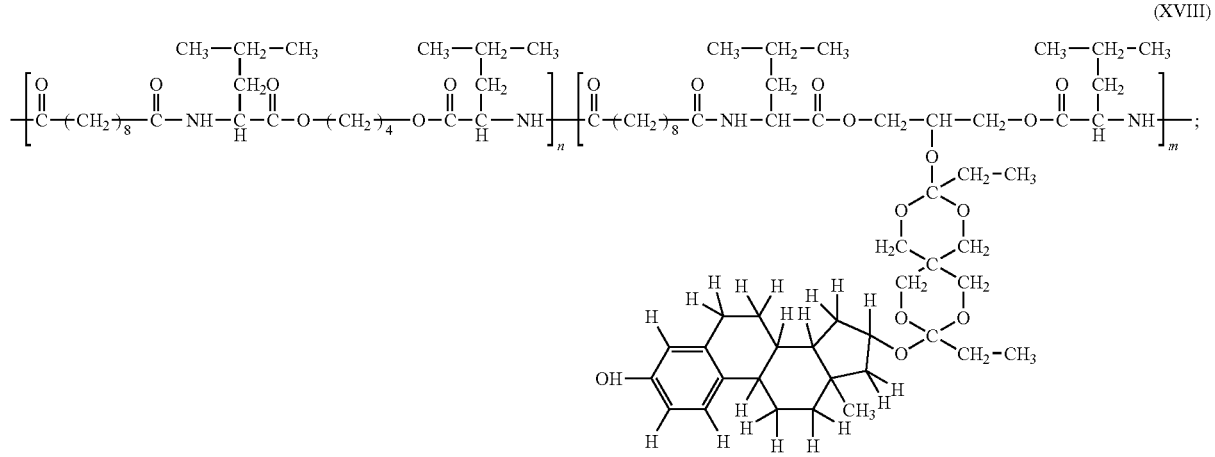

wherein n and m are integers not equal to 0. In formula (XVIII), the diol is butane-1,4-diol, the diacid is sebacic acid, one amino acid is leucine, the other amino acid is lysine, X is estradiol and $L_2$ is an orthoester known as 3,9-diethylidene-2,4,8,10-tetraoxaspiro-[5,5]-undecane (DETOSU), which is more labile than an ester.

To make the polymer, an oligo- or polyester-type diamino adduct can be made as described above, combining leucine and butane-1,4-diol. One equivalent of glycerol can be combined with two equivalents of leucine to obtain an amino-terminated polymeric subunit. Next, the polyester-type diamino adduct can be combined with sebacic acid and the amino-terminated polymeric subunit to obtain a hydroxy-functional PEA. Estradiol then can be combined with 3,9-diethylidene-2,4,8,10-tetraoxaspiro-[5,5]-undecane (DETOSU) to form an estradiol-DETOSU adduct. The hydroxy-functional PEA can be reacted with the estradiol-DETOSU adduct to form the PEA-agent combination.

A polymeric agent such as, for example, heparin can be connected to a PEA as a graft-copolymer. A PEA with pendant amino groups on the polymer backbone may be produced by a method that comprises polymerizing bis-(L-leucine)-1,6-hexylene diester with di-p-nitrophenyl sebacate and ε-carbobenzoxy-L-lysine in a suitable solvent such as, for example, DMF or THF. The temperature of the reaction ranges from about 25° C. to about 150° C., from about 50° C. to about 125° C., from about 80° C. to about 100° C., or any range therein. The reaction occurs for a time ranging from about 1 hour to about 24 hours, from about 6 hours to about 18 hours, from about 10 hours to about 14 hours, or any range therein. The carbobenzoxy protecting group can be removed with hydrogenolysis over a palladium on carbon catalyst using the method described above. A heparin-aldehyde adduct can be connected by reductive amination using sodium cyanoborohydride ($NaCNBH_3$) and a DMF/water solvent.

II. Agent as a Polymeric Block

A polymeric agent can be connected to a PEA as a block-copolymer. Examples of agents that can be incorporated into PEAs as polymeric blocks include, but are not limited to, heparin, hyaluronic acid, and poly(ethylene glycol)(PEG).

1. PEAs Comprising Heparin or Hyaluronic Acid Block(s)

A block-copolymer of PEA and heparin can be prepared by combining an amino-terminated PEA with a heparin-aldehyde adduct. An example of a heparin-aldehyde adduct is represented by a formula (XIX):

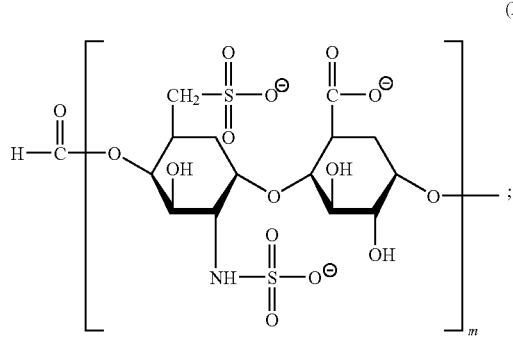

(XIX)

wherein m is an integer not equal to 0.

The heparin-aldehyde adduct can be combined with an amino-terminated PEA in a DMF/water solvent and subsequently reduced with NaCNBH$_3$ to produce the following PEA-heparin copolymer structure represented by formula (XX):

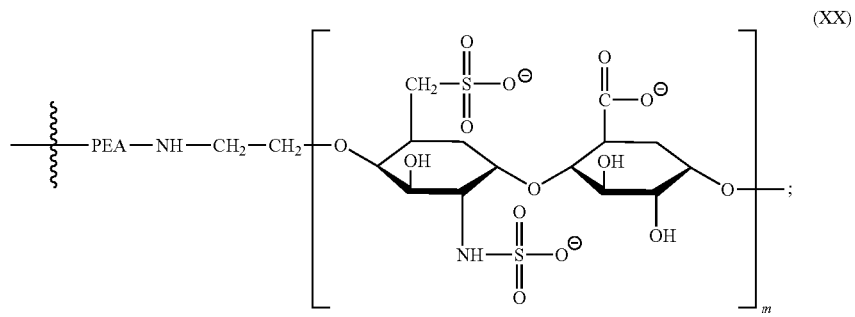

(XX)

wherein m is an integer not equal to 0.

One method of preparing the amino-terminated PEA comprises deviating from a one-to-one stoichiometry between the sum of the amino-terminated subunits and the diacids or diacid derivatives. To achieve the highest molecular weight, the stoichiometry of the diacids or diacid derivatives is kept at one-to-one with the sum of the amino-terminated subunits, because an excess of either component results in an amino-terminated PEA with a lower molecular weight.

Another method of preparing the amino-terminated PEA comprises keeping a one-to-one stoichiometry between the amino-terminated subunits and the diacids or diacid derivatives and the polymerization is allowed to proceed for a predetermined length of time. The polymerization is terminated by the introduction of an excess of a reactive diamine such as, for example, 1,4-butanediamine. All carboxyl endgroups are terminated and any unreacted diacids or diacid derivatives are consumed. Any low molecular weight material can be separated from the polymer by precipitating the polymer in a suitable solvent known to one of skill in the art.

The PEA-heparin copolymer shown above is an AB-block copolymer. The AB-type copolymers result when the two polymers only have a single active end. The method of the present invention can be designed to produce an AB copolymer, an ABA copolymer or an ABABAB . . . multi-block copolymer by activating either one or both ends of the agent polymer and the PEA polymer. Copolymers of the ABA-type result where one polymer has one active end and the other polymer has two active ends. Copolymers of the ABABAB . . . -type result where both polymers have two active ends.

A block-copolymer of PEA and heparin can be prepared by combining a carboxyl-terminated PEA with a heparin-aldehyde adduct. The heparin is first activated with, for example, EDC or DCC and then combined with a large excess of adipic dihydrazide to prepare an amino-functionalized heparin. Alternatively, a heparin-aldehyde adduct can be treated with ammonia or n-butylamine in the presence of a reducing agent such as, for example, sodium borohydride (NaBH$_4$), potassium borohydride (KBH$_4$), or NaCNBH$_3$. The carboxyl-terminated PEA is activated with, for example, EDC or DCC, and combined with the amino-functional heparin.

It should be appreciated that, in some embodiments of the present invention, the agent may be any biobeneficial agent that can enhance the biocompatibility or non-fouling properties of a PEA polymer. For example, hyaluronic acid can be a polymeric agent used to form a PEA-hyaluronic acid copolymer. Hyaluronic acid has free carboxyl groups, so a hyaluronic acid-aldehyde adduct can be made, for example, by oxidizing hyaluronic acid with nitrous acid or periodate. The hyaluronic-acid-aldehyde adduct can then be combined with a PEA as described above.

A PEA that is both carboxyl-terminated and amino-terminated can be analyzed using standard analytical techniques to determine a ratio of carboxyl groups to amino groups. Knowing this ratio will allow one skilled in the art to decide whether to connect the polymer agent to the amino ends of the PEA or to the carboxyl ends of the PEA. A skilled artisan can protect the amino groups on the PEA with, for example, acetic anhydride to reduce undesirable side conjugation when combining a carboxyl-terminated PEA with a heparin-aldehyde adduct.

2. Poly(ethylene glycol) Block(s)-Containing PEAs

A block copolymer of PEA and PEG can be prepared using a variety of techniques. In one embodiment, an amino-terminated PEA can be combined with a carboxyl-terminated PEG (Nektar Corp.) in the presence of, for example, EDC or DCC to form the following structure represented by a formula (XXI):

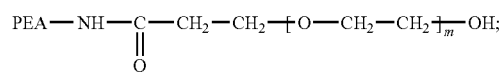

(XXI)

wherein m is an integer not equal to 0.

In another embodiment, either a succinimidyl derivative of mPEG (Nektar Corp.) or an isocyanate-terminated mPEG (Nektar Corp.) can be reacted with an amino-terminated PEA under conditions known to those of skill in the art. In another embodiment, the carboxyl group of a carboxyl-terminated PEA can be activated with, for example, EDC or DCC and combined with an amino-terminated mPEG (Nektar Corp.) In another embodiment, an amino-terminated mPEG can be combined with a high molecular weight PEA in the presence of an acid or base catalyst through amination of ester groups in a high molecular weight PEA. In another embodiment, an amino-terminated PEA can be combined with a methacrylate-terminated mPEG (Nektar Corp.) in the presence of an initiator capable of undergoing thermal or photolytic free radical decomposition. Examples of suitable initiators include benzyl-N,N-diethyldithiocarbamate or p-xylene-N,N-diethyldithiocarbamate. In another embodiment, an amino-terminated PEA can be combined with ethylene oxide in a living polymerization reaction, which is an unterminated anionic polymerization kept alive and controlled by maintaining a pure system. A living polymerization reaction can be killed through addition of a terminating agent such as, for example, water.

Forming a Coating

In some embodiments of the invention, the compositions are in the form of coatings for medical devices such as, for example, a balloon expandable stent or a self expanding stent. There are many coating configurations within the scope of the present invention, and each configuration can include any number and combination of layers. In some embodiments, the coatings of the present invention can comprise one or a combination of the following four types of layers:

(a) an agent layer, which may comprise a polymer and an agent or, alternatively, a polymer free agent;

(b) an optional primer layer, which may improve adhesion of subsequent layers on the implantable substrate or on a previously formed layer;

(c) an optional topcoat layer, which may serve as a way of controlling the rate of release of an agent; and (d) an optional biocompatible finishing layer, which may improve the biocompatibility of the coating.

In one embodiment, the agent layer can be applied directly to at least a part of an implantable substrate as a pure agent to serve as a reservoir for at least one bioactive agent. In another embodiment, the agent can be combined with a biodegradable polymer as a matrix, wherein agent may or may not be bonded to the polymer. In another embodiment, the optional primer layer can be applied between the implantable substrate and the agent layer to improve adhesion of the agent layer to the implantable substrate and can optionally comprise an agent. In another embodiment, a pure agent layer can be sandwiched between layers comprising biodegradable polymer. In another embodiment, the optional topcoat layer can be applied over at least a portion of the agent layer to serve as a membrane to control the rate of release of the bioactive agent and can optionally comprise agent. In another embodiment, the biocompatible finishing layer can also be applied to increase the biocompatibility of the coating by, for example, increasing acute hemocompatibility and can also comprise an agent. The inventive compositions can be used for one or any combination of these layers. In addition, in some embodiments, other polymers such as those previously mentioned (e.g., poly(butyl methacrylate), etc.) can be used as one of the layers or can be blended or crosslinked with the PEA embodiments.

Each layer can be applied to an implantable substrate by any method including, but not limited to, dipping, spraying, pouring, brushing, spin-coating, roller coating, meniscus coating, powder coating, inkjet-type application or a combination thereof. In one example, each of the layers can be formed on a stent by dissolving one or more biodegradable polymers, optionally with a non-biodegradable polymer, in one or more solvents and either (i) spraying the solution on the stent or (ii) dipping the stent in the solution. In this example, a dry coating of biodegradable polymer may be formed on the stent when the solvent evaporates. It should be appreciated that a process of forming a coating can include additional process steps such as, for example, the use of energy such as heat, electromagnetic radiation, electron beam, ion or charged particle beam, neutral-atom beam, and chemical energy.

The formation of each layer may involve use of a casting solvent. A casting solvent is a liquid medium within which a polymer can be solubilized to form a layer comprising that polymer on a substrate. The casting solvent must be selected to avoid adversely affecting an underlying material such as, for example, an underlying primer layer or a bare stent structure. In one example, a material used to form the primer layer is soluble in a highly polar casting solvent but is reasonably insoluble in a low polarity casting solvent. A material is "reasonably insoluble" in a solvent when the material does not solubilize to an extent great enough to significantly affect the performance of the resulting product, meaning that the product can still be used for its intended purpose. In this example, an overlying agent layer that is soluble in a low polarity casting solvent can be applied to the underlying primer layer without disrupting the structure of primer layer.

The casting solvent may be chosen based on several criteria including, for example, its polarity, molecular size, biocompatibility, reactivity and purity. Other physical characteristics of the casting solvent may also be taken into account including the solubility limit of the polymer in the casting solvent, the presence of oxygen and other gases in the casting solvent, the viscosity and vapor pressure of the combined casting solvent and polymer, the ability of the casting solvent to diffuse through an underlying material, and the thermal stability of the casting solvent. One of skill in the art has access to scientific literature and data regarding the solubility of a wide variety of polymers. Furthermore, one of skill in the art will appreciate that the choice of casting solvent may begin empirically by calculating the Gibb's free energy of dissolution using available thermodynamic data. Such calculations allow for a preliminary selection of potential solvents to test in a laboratory. It is recognized that process conditions can affect the chemical structure of the underlying materials and, thus, affect their solubility in a casting solvent. It is also recognized that the kinetics of dissolution are a factor to consider when selecting a casting solvent, because a slow dissolution of an underlying material, for example, may not affect the performance characteristics of a product where the product is produced relatively quickly.

Exemplary casting solvents for use in the present invention include, but are not limited to, DMAC, DMF, THF, cyclohexanone, xylene, toluene, acetone, i-propanol, methyl ethyl ketone, propylene glycol monomethyl ether, methyl butyl ketone, ethyl acetate, n-butyl acetate, and dioxane. Solvent mixtures can be used as well. Representative examples of the mixtures include, but are not limited to, DMAC and methanol (50:50 w/w); water, i-propanol, and DMAC (10:3:87 w/w); i-propanol and DMAC (80:20, 50:50, or 20:80 w/w); acetone and cyclohexanone (80:20, 50:50, or 20:80 w/w); acetone and xylene (50:50 w/w); acetone, xylene and FLUX REMOVER AMS® (93.7% 3,3-dichloro-1,1,1,2,2-pentafluoropropane and 1,3-dichloro-1,1,2,2,3-pentafluoropropane, and the balance is methanol with trace amounts of nitromethane; Tech Spray, Inc.) (10:40:50 w/w); and 1,1,2-trichloroethane and chloroform (80:20 w/w).

The following examples are provided to further illustrate embodiments of the present invention.

Example 1

The PEA of formula (XVII) can be prepared according to the following procedure:

Method of Preparing of L-Leucine-ε-L-Lysine Benzyl Ester-2TosOH

L-leucine-ε-L-lysine-HCl (New England Peptide, Inc.) (73.86 gm, 0.25 mole), p-toluenesulfonic acid (152.15 gm, 0.80 mole), benzyl alcohol (100.9 ml, 0.97 mole), and 200 ml of benzene is added to a 1 liter reaction flask equipped with a mechanical stirrer, Dean Stark trap, thermometer and argon inlet. The mixture is heated to 80° C. for 8 hours, and condensate is collected in the Dean Stark trap. The mixture is transferred to a 2 liter flask, and 1 liter of ethyl acetate is added to the mixture with stirring. The mixture is stored overnight at 4° C., and L-Leucine-ε-L-Lysine Benzyl Ester-2TosOH and is isolated by filtration.

Method of Preparing co-poly-{[N,N'-sebacoyl-bis-(L-leucine)-1,6-hexylene diester]-[N,N'-sebacoyl-L-leucine-L-lysine mPEG amide]}

Dry triethylamine (61.6 ml, 0.44 mole) is added to a mixture of di-p-toluenesulfonic acid salt of bis-(L-leucine)-1,6-hexylene diester (120.4 gm, 0.18 mole), di-p-toluenesulfonic acid salt of L-leucine-ε-L-lysine benzyl ester (13.863 gm, 0.02 mole), and di-p-nitrophenyl sebacinate (88.88 gm, 0.2 mole) in dry DMAC (110 ml). The mixture is stirred and heated at 80° C. for 12 hours. The mixture is then cooled to room temperature, diluted with ethanol (300 ml), and poured into 1 liter of water. The polymer is separated, washed with water, and vacuum dried, A free carboxyl group is generated by hydrogenolysis over a palladium catalyst. Ethanol (1200 ml) and the polymer (100 mg) is added to a 2 liter flask with a palladium on carbon catalyst (5 gm) (Aldrich). Hydrogen is bubbled and stirred through the mixture for 24 hours, and the palladium on carbon catalyst is separated by centrifugation to leave an isolated solution.

The isolated solution is added to hexane/ethyl acetate (10 liters of a 50/50 mixture) with stirring to precipitate co-poly-{[N,N'-sebacoyl-bis-(L-leucine)-1,6-hexylene diester]-[N,N'-sebacoyl-L-leucine-L-lysine]}. The polymer is filtered, dissolved (50 gm) in THF (1500 ml) in a 2 liter flask with stirring and an argon purge, and then combined with N-hydroxysuccinimide (1.32 gm, 0.0115 mole) and dicyclohexylcarbodiimide (2.37 gm, 0.0115 mole). The combination is stirred for 24 hours at ambient temperature and filtered to remove 1,3-dicyclohexylurea. The filtered solution is combined with an amino-terminated mPEG (MW 5000, 46 gm, 0.0092 moles) (Nektar Corp.) in a 2 liter flask and stirred for 6 hours under argon. The co-poly-{[N,N'-sebacoyl-bis-(L-leucine)-1,6-hexylene diester]-[N,N'-sebacoyl-L-leucine-L-lysine mPEG amide]} is precipitated by slow addition of the solution into hexane/ethyl acetate (50/50) with stirring. While not intending to be bound by any theory or mechanism of action, a proposed reaction mechanism for the preparation of the poly(ester amide) (PEA) of formula (XVII) according to one embodiment of the present invention is illustrated in FIG. 1.

Example 2

Figure 2:
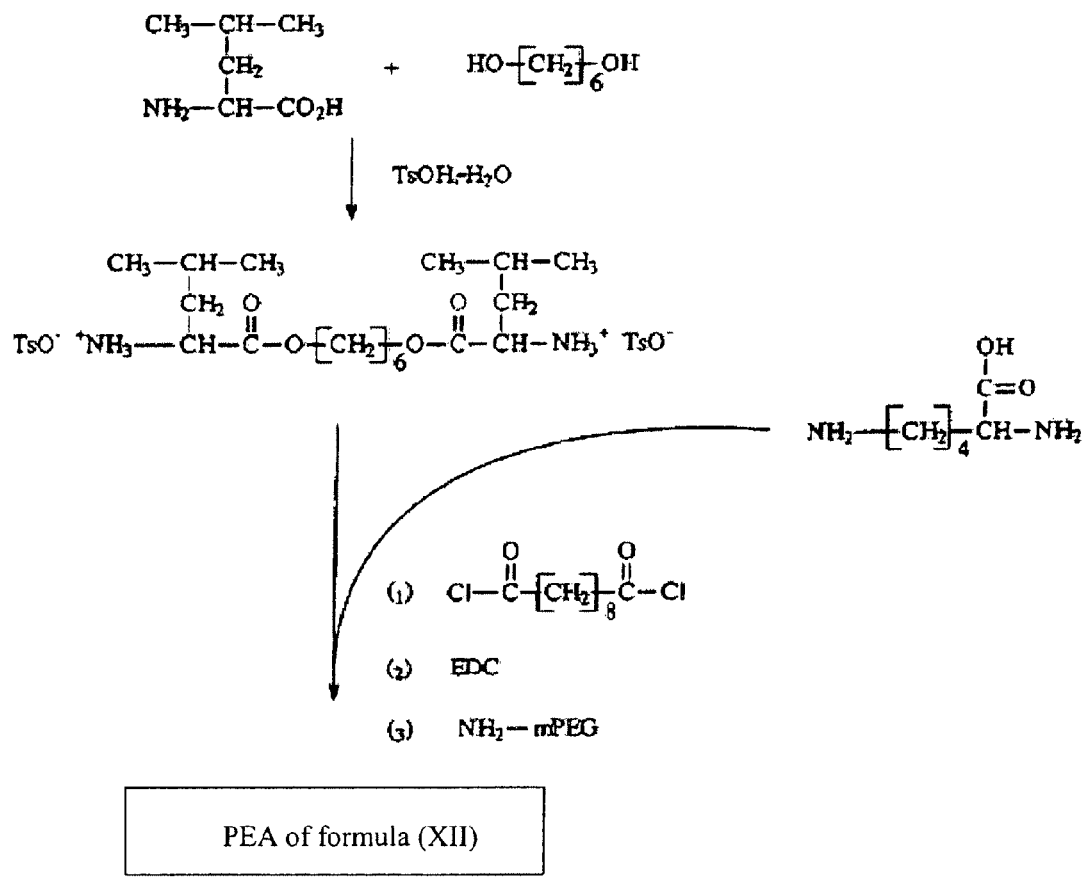
FIG. 2 illustrates a proposed reaction mechanism for the preparation of the PEA of formula (XII) according to one embodiment of the present invention.

The copolymer represented by formula (XII) can be prepared in a manner analogous to the method used to prepare the copolymer represented by formula (XVII) by replacing the L-leucine-ε-L-lysine-HCl with L-lysine HCl. While not intending to be bound by any theory or mechanism of action, a proposed reaction mechanism for the preparation of the PEA of formula (XII) according to one embodiment of the present invention is illustrated in FIG. 2.

Example 3

The PEA of formula (XV) can be prepared according to the following procedure:

Method of Preparing co-poly-{[N,N'-sebacoyl-bis-(L-leucine)-1,4-butylene diester]-[N,N'-sebacoyl-L-lysine-4-carboxy-TEMPO anhydride]}

Dry triethylamine (61.6 ml, 0.44 mole) is added to a mixture of a di-p-toluenesulfonic acid salt of bis-(L-leucine)-1, 4-butylene diester (118.82 gm, 0.18 mole), a di-p-toluenesulfonic acid salt of L-lysine benzyl ester (11.603 gm, 0.02 mole), and di-p-nitrophenyl sebacinate (88.88 gm, 0.2 mole) in dry DMAC (110 ml). The mixture is stirred and heated at 80° C. for 12 hours, cooled to room temperature, diluted with ethanol (300 ml), and poured into water (1 liter). The polymer is separated, washed with water, and dried under vacuum. A free carboxyl group can be generated by hydrogenolysis over a palladium catalyst. Ethanol (1200 ml) is combined with the polymer (100 gm) and a palladium on carbon catalyst in a 2 liter flask (Aldrich). Hydrogen is bubbled and stirred through the solution for 24 hours. The palladium on carbon is separated by centrifugation to leave an isolated solution. The isolated solution is slowly added to hexane/ethyl acetate (10 liters, 50/50) with stirring to precipitate co-poly-{[N,N'-sebacoyl-bis-(L-leucine)-1,6-hexylene diester]-[N,N'-sebacoyl-L-lysine]}. The polymer (50 gm) is filtered, dissolved and stirred in dry 1,1,2-trichloroethane (1600 ml) in a 2 liter flask, and acetic anhydride (2.24 gm, 0.022 mole) and 4-carboxyl-TEMPO (4.01 gm, 0.02 mole) is added to the 2 liter flask. The mixture is distilled under vacuum to remove DMF at 80° C. and a sufficient amount of heat is applied to achieve a distillation rate of about 5 ml/min. The solution is stirred for two hours, cooled to room temperature, and the co-poly-{[N, N'-sebacoyl-bis-(L-leucine)-1,4-butylene diester]-[N,N'-sebacoyl-L-lysine-4-carboxy-TEMPO anhydride]} is precipitated by slow addition of the solution to hexane/ethyl acetate (4 liters, 50/50) with stirring.

Example 4

The PEA of formula (XVIII) can be prepared according to the following procedure:

Method of Preparing Conjugate of estradiol and 3,9-diethylidene-2,4,8,10-tetraoxaspiro-[5,5]-undecane (DETOSU)

Dry THF (40 ml) is combined with DETOSU (5 gm, 0.0236 mole) and six drops of 1% p-toluenesulfonic acid in THF in a 100 ml flask. A solution of estradiol (6.42 gm. 0.0236 mole) in THF (20 ml) is slowly added with stirring for over an hour. The estradiol-DETOSU conjugate is isolated by rotary evaporation.

Method of Preparing bis-(L-leucine)-1,3-propylene diester-2-one

L-leucine (32.80 gm, 0.25 mole), p-toluenesulfonic acid (104.6 gm, 0.55 mole), 1,3-dihydroxy acetone dimer (22.53 gm, 0.125 mole), and 200 ml of benzene are added to a 1 liter flask. The solution is heated at 80° C. for 8 hours, and condensate is collected in a Dean Stark trap. The solids are separated from the solvents by rotoevaporation, rinsed in Buchner funnel with water (2, 1 liter portions) and dried in a vacuum oven.

Method of Preparing co-poly-{[N,N'-sebacoyl-bis-(L-leucine)-1,4-butylene diester]-[N,N'-sebacoyl-bis-L-leucine-1,3-propylene diester-2-one]}

Dry triethylamine (61.6 ml, 0.44 mole) is added to a mixture of a di-p-toluenesulfonic acid salt of bis-(L-leucine)-1,4-butylene diester (118.82 gm, 0.18 mole), a di-p-toluenesulfonic acid salt of bis-(L-leucine)-1,3-propylene diester-2-one (13.20 gm, 0.02 mole), and di-p-nitrophenyl sebacinate (88.88 gm, 0.2 mole) in dry DMAC (110 ml). The mixture is stirred and heated at 80° C. for 12 hours, cooled to room temperature, diluted with ethanol (300 ml), and poured into water (1 liter). The polymer is separated, washed with water, and dried under a vacuum. The polymer (80.35 gm), dry THF (250 ml), sodium cyanoborohydride (10.49 gm, 0.167 mole), and p-touluenesulfonic acid (6 drops of a 1% solution) in THF is added to a 500 ml flask. The mixture is stirred for two hours at ambient temperature, poured into chloroform (500 ml), and extracted with 3 portions of aqueous sodium bicarbonate (250 ml, 1M portions). Chloroform is removed by rotoevaporation and the remaining solvent is removed by drying overnight in a vacuum oven at ambient temperature. The polymer (60 gm), dry THF (250 ml), and the estradiol-DETOSU conjugate (6.64 gm, 0.0137 mole) is added to a 500 ml flask and stirred at room temperature for two hours. The polymer is precipitated by slow addition of the solution into hexane/ethyl acetate (2 liters, 50/50) with stirring.

Example 5

Method of preparing an Amino-Terminated PEA or a Carboxyl-Terminated PEA

The monomers used in a preparation of PEA provide a roughly 50/50 distribution between amino and activated carboxy-terminated chains at any point during the polymerization. Amino-terminated PEAs can be prepared using a biocompatible, low molecular weight chain-stopper, 1,4-diaminobutane (putrescine) that is added in a large excess to terminate all chains with amino groups at the end of the polymerization, or when the polymerization has reached the desired molecular weight. Carboxyl-terminated PEAs can be prepared by several methods. In one method, a dicarboxylic acid compound such as, for example, di-p-nitrophenyl sebacinate, can be combined with the PEA in excess. This embodiment is simple, but it has a potential drawback of lowering the final molecular weight of the polymer. Another method is to further derivatize a PEA containing a 50/50 distribution of amino-terminated and activated-carboxyl-terminated chains by reacting the PEA with a reagent such as, for example, succinic anhydride, to convert amino groups to carboxyl groups.

Method of preparing an Amino-Terminated co-poly-{[N,N'-sebacoyl-bis-(L-leucine)-1,6-hexylene diester]-[N,N'-sebacoyl-L-lysine benzyl ester]}

Dry triethylamine (61.6 ml, 0.44 mole) is added to a mixture of a di-p-toluenesulfonic acid salt of bis-(L-leucine)-1,6-hexylene diester (123.86 gm, 0.18 mole), a di-p-toluenesulfonic acid salt of L-lysine benzyl ester (11.603 gm, 0.02 mole), and di-p-nitrophenyl sebacinate (88.88 gm, 0.2 mole) in dry DMAC (110 ml). The mixture is stirred and heated at 80° C. for 4 hours, at which point 1,4-diaminobutane (15 gm, 0.17 mole) is added and the mixture is stirred at 80° C. for an additional hour. The solution is cooled to room temperature, diluted with ethanol (300 ml), and poured into a phosphate buffer (2 liters, 0.1 M, pH 7). The polymer is collected by filtration, suspended in chloroform (1 liter), and extracted with 3 portions of phosphate buffer (0.1 M, pH 7, 1 liter portions). The chloroform is removed by rotary evaporation, and the amino-terminated co-poly-{[N,N'-sebacoyl-bis-(L-leucine)-1,6-hexylene diester]-[N,N'-sebacoyl-L-lysine benzyl ester]} is dried overnight in a vacuum oven at ambient temperature.

Method of preparing an Carboxy-Terminated co-poly-{[N,N'-sebacoyl-bis-(L-leucine)-1,6-hexylene diester]-[N,N'-sebacoyl-L-lysine benzyl ester]}

Dry triethylamine (61.6 ml, 0.44 mole) is added to a mixture of a di-p-toluenesulfonic acid salt of bis-(L-leucine)-1,6-hexylene diester (123.86 gm, 0.18 mole), a di-p-toluenesulfonic acid salt of L-lysine benzyl ester (11.603 gm, 0.02 mole), and di-p-nitrophenyl sebacinate (88.88 gm, 0.2 mole) in dry DMAC (110 ml). The mixture is stirred and heated at 80° C. for 4 hours, at which point succinic anhydride (17 gm, 0.17 mole) is added and the mixture is stirred at 80° C. for an additional hour. The solution is cooled to room temperature, diluted with ethanol (300 ml), and poured into a phosphate buffer (2 liters, 0.1 M, pH 7). The polymer is collected by filtration, suspended in chloroform (1 liter), and extracted with 3 portions of phosphate buffer (0.1 M, pH 7, 1 liter portions). The chloroform is removed by rotoevaporation, and the carboxy-terminated co-poly-{[N,N'-sebacoyl-bis-(L-leucine)-1,6-hexylene diester]-[N,N'-sebacoyl-L-lysine benzyl ester]} is dried overnight in a vacuum oven at ambient temperature. This preparation can result in a polymer wherein all of the endgroups are carboxyl, and some of the endgroups are still activated with a p-nitrophenol group. This group may be suitable for subsequent coupling steps such as with, for example, an amino-terminated moiety. If it is desired to convert all endgroups to free carboxylic endgroups, the following steps would be inserted into the synthesis: after the addition of the succinic anhydride and stirring for one hour, L-leucine (11.2 gm, 0.085 mole) and triethylamine (8.59 gm, 0.085 mole) would be added and stirred for an additional hour.

Example 6

Method of Preparing a PEA-Heparin Conjugate by Combining Heparin with an Amino-Terminated PEA A PEA-heparin conjugate can be prepared by connecting an amino-terminated PEA with a heparin-aldehyde adduct formed by oxidative cleavage of heparin. An amino-terminated PEA (50 g) is added to a reactor containing DMAC/water (1 liter, 40:1) under nitrogen. A heparin-aldehyde adduct (7.5 g) and cyanoborohydride (0.2 g; 3.2 mmol) is added to the solution and heated to 60° C. for 12 hours under nitrogen, cooled to room temperature, and added dropwise to methanol. The PEA-heparin conjugate is filtered, washed with 3 portions of water (250 mL portions), and dried under vacuum.

Alternate Method of Preparing a PEA-Heparin Conjugate by EDC Coupling of a D-glucoronic Acid or L-iduronic Acid Functionality of the Heparin in a DMAC/Water Medium Heparin (20 g) is combined with a DMAC/water solution (450 g) and N-(3'-dimethylaminopropyl)-N'-ethylcarbodiimide (0.2 g, 1.0 mmol). The solution is stirred at room temperature for 2 hours under nitrogen, and the PEA-amine (50 g) is added to the DMAC/water solution (40/1; 500 g) and mixed at pH 4.75 for 4 hours. The solution is neutralized with sodium hydroxide (0.1 M) to pH 7.5 and stirred overnight under nitrogen. The PEA-heparin conjugate is precipitated by addition of the solution into THF, filtered and washed with water.

Example 7

Method of Preparing a PEA-PEG Conjugate with an Amino-Terminated PEA

An amino-terminated PEA can be PEGylated by aldehyde coupling/imine reduction, carbodiimide coupling of a carboxyl terminated PEG, and maleimide coupling of a PEG-maleimide to an amine terminated PEA.

An amino-terminated PEA can be conjugated to PEG by aldehyde coupling/imine reduction. A PEA (50 g) is dissolved in anhydrous DMAC (230 g) in the coupling of PEG to amino-terminated PEA. A PEG-butyraldehyde (MW 1000-50,000, 7.5 g) is combined with sodium cyanoborohydride (1.0 g) and stirred overnight at room temperature under nitrogen. The polymer is precipitated by addition of the solution with stirring in methanol, redissolved in DMAC, reprecipitated in water, and dried under vacuum.

An amino-terminated PEA can be conjugated to PEG by carbodiimide coupling of a carboxyl terminated PEG using DCC/NHS coupling. An amino-terminated PEA (50 g) is added to anhydrous THF (116 g; 1-35% w/w). Anhydrous THF (116 g) and carboxyl-terminated PEG (10 kD, 7.0 g, 0.7 mmol), dicyclohexylcarbodiimide (0.15 g; 7.1 mmol) (DCC) is added to a reactor containing N-hydroxysuccinimide (0.10 g/8 mmol) (NHS) to form a mixture. The mixture is stirred under nitrogen for 2 hours at room temperature, and the amino-terminated PEA solution is added to the mixture in a dropwise manner, stirred overnight at room temperature, and added dropwise to methanol to form a PEA-PEG precipitate. The precipitate is filtered and dried under vacuum.

Example 8

A medical article with two layers was fabricated to comprise everolimus by preparing a first composition and a second composition, wherein the first composition was an agent layer comprising a matrix of PEA and agent, and the second composition was a PEA topcoat layer. The first composition was prepared by mixing about 2% (w/w) co-poly-{[N,N'-sebacoyl-bis-(L-leucine)-1,6-hexylene diester]-[N,N'-sebacoyl-L-lysine benzyl ester]} ("example PEA") and about 0.5% (w/w) everolimus in absolute ethanol, sprayed onto a surface of a bare 12 mm VISION™ stent (Guidant Corp.) ("example stent") and dried to form a coating. An example coating technique comprised spray-coating with a 0.014 fan nozzle, a feed pressure of about 0.2 atm and an atomization pressure of about 1.3 atm; applying about 20 μg of wet coating per pass; drying the coating at about 50° C. for about 10 seconds between passes and baking the coating at about 50° C. for about 1 hour after the final pass to form a dry agent layer. The agent layer was comprised of about 428 μg of PEA and about 107 μg of everolimus. The second composition was prepared by mixing about 2% (w/w) of the example PEA in absolute ethanol and applied using the example coating technique. The topcoat layer contained about 300 μg of the example PEA. The total weight of the coating was about 835 μg.

Example 9

A medical article with three layers was fabricated to comprise everolimus by preparing a first composition, a second composition and a third composition. The first composition was a primer layer of PEA. The second composition was a pure agent layer, and the third composition was a topcoat layer of PEA. The first composition was prepared by mixing about 2% (w/w) of the example PEA in absolute ethanol and applied onto the surface of the example stent using the example coating technique to form a dry primer layer. The dry primer layer contained about 100 μg of the example PEA. The second composition was prepared by mixing about 2% (w/w) everolimus in absolute ethanol and applied to the primer layer using the example coating technique to form a pure agent layer comprising about 107 μg of everolimus. The third composition was prepared by mixing about 2% (w/w) of the example PEA in absolute ethanol and applied using the example coating technique to form a topcoat layer comprising about 300 μg of the example PEA. The total weight of the coating was about 507 μg.

Example 10

The coatings prepared and formed in Examples 8 and 9 were tested for total recovery of the bioactive agent, which is a measure of the percentage of bioactive agent extracted from the stent. The effects of sterilization were determined. A total of 32 stents were coated as described in Examples 8 and 9: 16 stents were coated as described in Example 8, wherein 8 stents were sterilized with electronic beam sterilization, and 8 stents were not sterilized; 16 stents were coated as described in Example 9, wherein 8 stents were sterilized using electronic beam sterilization, and 8 stents were not sterilized.

The coated stents were placed in a volumetric flask with acetonitrile comprising about 0.02% (w/w) butylated hydroxytoluene protectant ("extraction solvent") and sonicated for about 30 minutes to yield an extract of bioactive agent. The extract was analyzed with high pressure liquid chromatography (Waters 2690 HPLC system equipped with an analytical pump, a YMC Pro C18 separation column with an ultra-pure, silica-based adsorbent with 3 μm particles, an automatic sampler, and a 996 PAD (photodiode array detector) maintained at about 40° C.) ("the example HPLC method"). The mobile phase was fed into the column at a flow rate of about 1 ml/min and comprised about 71% (w/w) acetonitrile in 20 mM ammonium acetate solution.

The sterilized stents of Example 8 released about 91% of the everolimus, whereas the non-sterilized stents of Example 8 released about 100% of the everolimus. The sterilized stents of Example 9 released about 89% of the everolimus, whereas the non-sterilized stents of Example 9 released about 96% of the everolimus.

Example 11

The coatings prepared and formed in Examples 8 and 9 were tested for in vitro release of everolimus. The in vitro conditions were simulated in a buffer solution containing TRITON® X-100 and a porcine serum.

The simulations involved placing the coated stents on a VanKel Bio-Dis release rate tester (Varian, Inc.) and dipping the stents at a rate of 40 dips per minute into about 7 ml of 10 mM phosphate buffer saline solution (pH=7.4) containing about 1% (w/w) TRITON® X-100 (Sigma-Aldrich Corp.) at a temperature of about 37° C. The test was conducted in predetermined time increments of about 1, 2, 6, 9, 24, and 29 hours, and the amount of everolimus was measured using the example HPLC method. A fresh buffer solution was used for each measurement.

Figure 3:
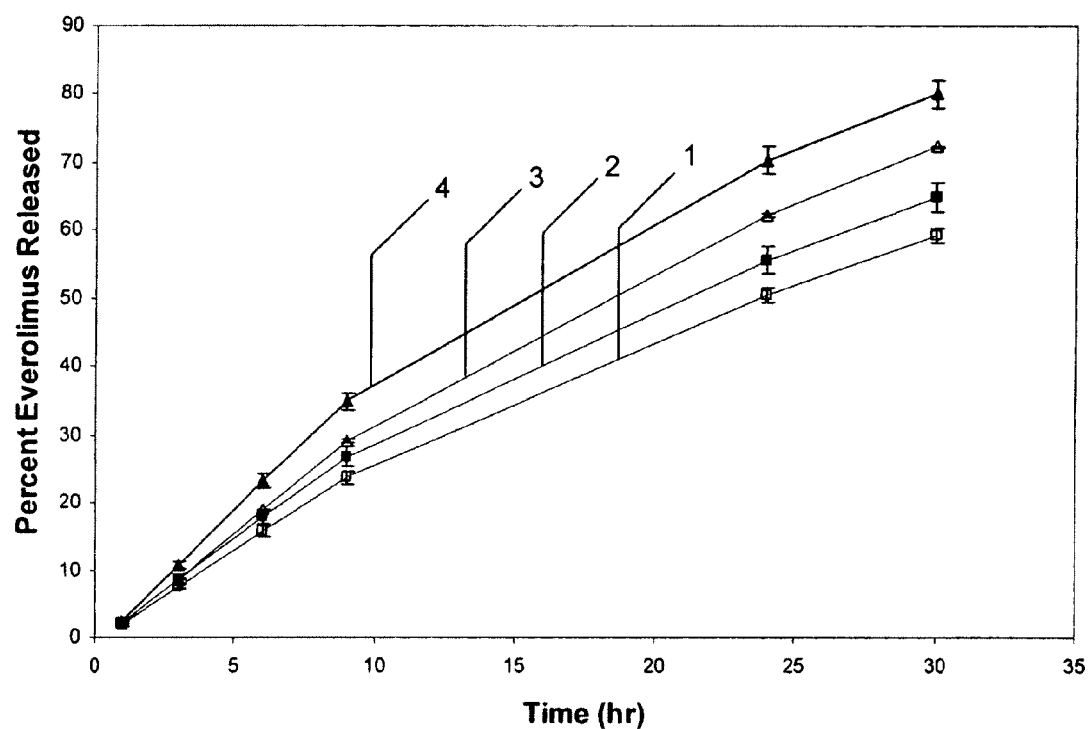
FIG. 3 illustrates the percent everolimus released in a buffer solution containing TRITON® X-100 from stent coatings that were designed according to embodiments of the present invention.

FIG. 3 illustrates the percent everolimus released in a buffer solution containing TRITON® X-100 from stent coatings that were designed according to embodiments of the present invention. Curve 1 illustrates the everolimus released from the non-sterile stent coatings of Example 8. Curve 2 illustrates the everolimus released from the sterile stent coatings of Example 8. Curve 3 illustrates the everolimus released from the non-sterile stent coatings of Example 9. Curve 4 illustrates the everolimus released from the sterile stent coatings of Example 9. The release rate profiles were uniform, and the coatings of Example 8 released everolimus at a slower rate than the coatings of Example 9. Sterilization increased the release rate by about 10 to 25% in the coatings of Example 9 and by about 10 to 15% in the coatings of Example 8.

The porcine serum simulations involved the same method and replaced the buffer solution containing TRITON® X-100 with about 10 ml of porcine serum containing about 0.1% (w/w) sodium azide. The used porcine serum was replaced with the fresh porcine serum every 8 hours, and the temperature of the solution was maintained at about 37° C. The amount of everolimus remaining on the stents after 24 hours was measured using the example HPLC method. The amount of everolimus released was calculated by subtracting the amount of everolimus remaining on the stent from the amount of everolimus initially deposited on the stent. Table 4 contains a summary of the release rate results.

TABLE 4

| Example | Sterilized (S) Non-sterilized (NS) | Average In Vitro Release of Everolimus (over 24 hours, at 37° C., % ± std. dev. (w/w)) | |
|---|---|---|---|
| | | TRITON ® X-100 Buffer Solution | Porcine Serum |
| 8 | S | 55.63 ± 2.06 | 33.35 ± 1.99 |
| 8 | NS | 50.41 ± 1.05 | 31.68 ± 1.22 |
| 9 | S | 70.30 ± 1.98 | 37.95 ± 5.46 |
| 9 | NS | 62.34 ± 0.27 | 34.96 ± 1.81 |

Table 4 illustrates that the amount of everolimus released over 24 hours from the coatings of Example 8 was less than that released from the coatings of Example 9 in both the buffer solution containing TRITON® X-100 and in the porcine serum. The amount of everolimus released from the sterilized coatings was higher than that released from the corresponding non-sterilized coatings in both cases.

While particular embodiments of the present invention have been shown and described, it will be obvious to those skilled in the art that changes and modifications can be made to the present invention without departing from the spirit and scope of the invention. For example, a multitude of chemical structures, polymers, and agents have been listed herein. One of skill in the art is to appreciate that such listings are provided by way of example only, and are not intended to limit the scope of the invention.

We claim:

1. A coating for an implantable medical device comprising a polymer of formula:

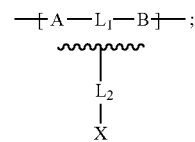

wherein A is

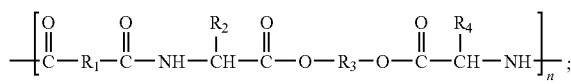

B is

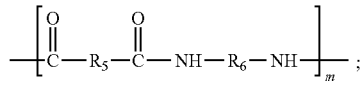

wherein the polymer is amino-terminated or carboxy-terminated;

where $R_1$ and $R_5$ are optional and are independently selected from the group consisting of substituted, unsubstituted, hetero-, straight-chained, branched, cyclic, saturated and unsaturated aliphatic radicals; and substituted, unsubstituted, and hetero-aromatic radicals;

$R_3$ is selected from the group consisting of substituted, unsubstituted, hetero-, straight-chained, branched, cyclic, saturated and unsaturated aliphatic radicals; and substituted, unsubstituted, and hetero-aromatic radicals;

$R_2$, $R_4$ and $R_7$ are independently selected from the group consisting of hydrogen; substituted, unsubstituted, hetero-, straight-chained, branched, cyclic, saturated and unsaturated aliphatic radicals; and substituted, unsubstituted, and hetero-aromatic radicals;

$R_6$ is selected from the group consisting of substituted, unsubstituted, hetero-straight-chained and branched aliphatic radicals;

$L_1$ is an optional linkage connecting A to B and, if present, comprises a disulfide, poly(ethylene glycol), methoxy-poly(ethylene glycol), poly(ethylene oxide), poly(propylene glycol), poly(tetramethylene glycol), poly(ethylene oxide-co-propylene oxide), or a copolymer thereof;

X is a biobeneficial agent selected from the group consisting of poly(alkylene glycols), methoxypoly(ethylene glycol), poly(N-vinyl pyrrolidone), poly(acrylamide methyl propane sulfonic acid), poly(styrene sulfonate), sulfonated dextran, polyphosphazenes, poly(orthoesters), poly(tyrosine carbonate), hyaluronic acid, heparin, a graft copolymer of poly(L-lysine) and poly(ethylene glycol), and salts, copolymers and combinations thereof; a free radical scavenger, a nitric oxide donor, rapamycin, tacrolimus, paclitaxel, docetaxel, estradiol, clobetasol, idoxifene, tazarotene, and salts and combinations thereof; antiproliferatives, antineoplastics, antimitotics, anti-inflammatories, antiplatelets, anticoagulants, antifibrins, antithrombins, antibiotics, antiallergics, antioxidants, and salts and combinations thereof; 40-O-(2-hydroxy)ethyl-rapamycin (everolimus), 40-O-(3-hydroxypropyl)-rapamycin, 40-O-[2-(2-hydroxy)ethoxy]ethyl-rapamycin, and salts and combinations thereof;

L₂ is a linkage connecting X to the polymer; and n and m are independently integers not equal to 0.

2. An implantable medical device comprising a polymer of formula:

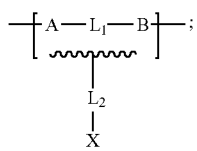

wherein A is

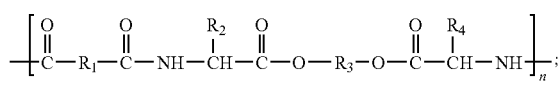

B is

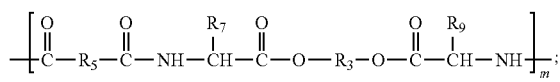

wherein the polymer is amino-terminated or carboxy-terminated;

where R₁ and R₅ are optional and are independently selected from the group consisting of substituted, unsubstituted, hetero-, straight-chained, branched, cyclic, saturated and unsaturated aliphatic radicals; and substituted, unsubstituted, and hetero-aromatic radicals;

R₃ is selected from the group consisting of substituted, unsubstituted, hetero-, straight-chained, branched, cyclic, saturated and unsaturated aliphatic radicals; and substituted, unsubstituted, and hetero-aromatic radicals;

R₂, R₄ and R₇ are independently selected from the group consisting of hydrogen; substituted, unsubstituted, hetero-, straight-chained, branched, cyclic, saturated and unsaturated aliphatic radicals; and substituted, unsubstituted, and hetero-aromatic radicals;

R₆ is selected from the group consisting of substituted, unsubstituted, hetero-, straight-chained and branched aliphatic radicals;

L₁ is an optional linkage connecting A to B and, if present, comprises a disulfide, poly(ethylene glycol), methoxypoly(ethylene glycol), poly(ethylene oxide), poly(propylene glycol), poly(tetramethylene glycol), poly(ethylene oxide-co-propylene oxide), or a copolymer thereof;

X is a biobeneficial agent selected from the group consisting of poly(alkylene glycols), methoxypoly(ethylene glycol), poly(N-vinyl pyrrolidone), poly(acrylamide methyl propane sulfonic acid), poly(styrene sulfonate), sulfonated dextran, polyphosphazenes, poly(orthoesters), poly(tyrosine carbonate), hyaluronic acid, heparin, a graft copolymer of poly(L-lysine) and poly(ethylene glycol), and salts, copolymers and combinations thereof; a free radical scavenger, a nitric oxide donor, rapamycin, tacrolimus, paclitaxel, docetaxel, estradiol, clobetasol, idoxifene, tazarotene, and salts and combinations thereof; antiproliferatives, antineoplastics, antimitotics, anti-inflammatories, antiplatelets, anticoagulants, antifibrins, antithrombins, antibiotics, antiallergics, antioxidants, and salts and combinations thereof; 40-O-(2-hydroxy)ethyl-rapamycin (everolimus), 40-O-(3-hydroxypropyl)-rapamycin, 40-O-[2-(2-hydroxy)ethoxy]ethyl-rapamycin, and salts and combinations thereof;

L₂ is a linkage connecting X to the polymer; and n and m are independently integers not equal to 0.

3. A method for fabricating an implantable medical device of claim 2, comprising:

(a) preparing a polymer represented by a formula:

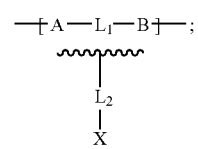

wherein A is

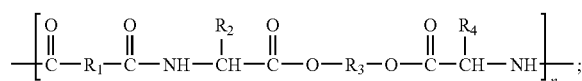

B is

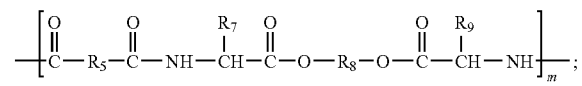

wherein the polymer is amino-terminated or carboxy-terminated;

where R₁ and R₅ are optional and are independently selected from the group consisting of substituted, unsubstituted, hetero-, straight-chained, branched, cyclic, saturated and unsaturated aliphatic radicals; and substituted, unsubstituted, and hetero-aromatic radicals;

R₃ is selected from the group consisting of substituted, unsubstituted, hetero-, straight-chained, branched, cyclic, saturated and unsaturated aliphatic radicals; and substituted, unsubstituted, and hetero-aromatic radicals;

R₂, R₄, and R₇ are independently selected from the group consisting of hydrogen; substituted, unsubstituted, hetero-, straight-chained, branched, cyclic, saturated and unsaturated aliphatic radicals; and substituted, unsubstituted, and hetero-aromatic radicals;

R₆ is selected from the group consisting of substituted, unsubstituted, hetero-, straight-chained and branched aliphatic radicals;

L₁ is an optional linkage connecting A to B and, if present, comprises a disulfide, poly(ethylene glycol), methoxypoly(ethylene glycol), poly(ethylene oxide), poly(propylene glycol), poly(tetramethylene glycol), poly(ethylene oxide-co-propylene oxide), or a copolymer thereof;

X is a biobeneficial agent selected from the group consisting of poly(alkylene glycols), methoxypoly(ethylene glycol), poly(N-vinyl pyrrolidone), polyacrylamide methyl propane sulfonic acid), poly(styrene sulfonate), sulfonated dextran, polyphosphazenes, poly(orthoesters), poly(tyrosine carbonate), hyaluronic acid, heparin, a graft copolymer of poly(L-lysine) and poly(ethylene glycol), and salts, copolymers and combinations thereof; a free radical scavenger, a nitric oxide donor, rapamycin, tacrolimus, paclitaxel, docetaxel, estradiol, clobetasol, idoxifene, tazarotene, and salts and combinations thereof; antiproliferatives, antineoplastics, antimitotics, anti-inflammatories, antiplatelets, anticoagulants, antifibrins, antithrombins, antibiotics, antiallergics, antioxidants, and salts and combinations thereof; 40-O-(2-hydroxy)ethyl-rapamycin (everolimus), 40-O-(3-hydroxypropyl)-rapamycin, 40-O-[2-(2-hydroxy)ethoxy]ethyl-rapamycin, and salts and combinations thereof;

$L_2$ is a linkage connecting X to the polymer;

n and m are independently integers not equal to 0; and (b) forming a coating comprising the polymer on at least a portion of an implantable substrate.

4. The method of claim 3, wherein the polymer is represented by a formula:

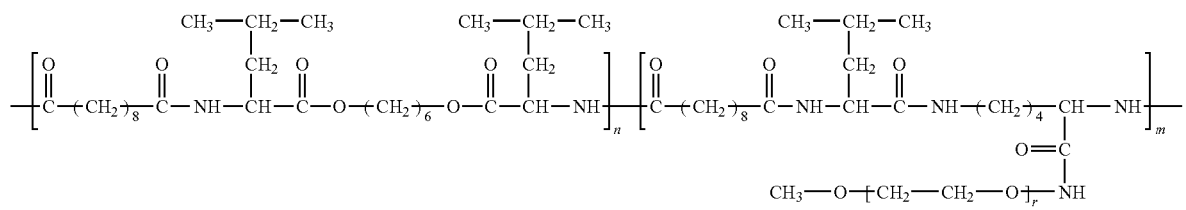

wherein n, m and r are independently integers not equal to zero.

5. A stent comprising a coating, wherein the coating comprises a polymer of formula:

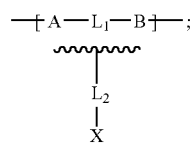

wherein A is

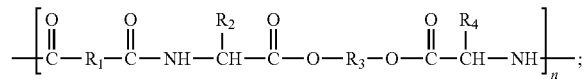

B is

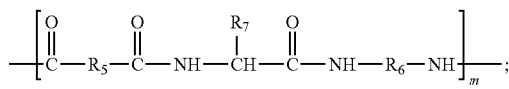

wherein the polymer is amino-terminated or carboxy-terminated;

where $R_1$ and $R_5$ are optional and are independently selected from the group consisting of substituted, unsubstituted, hetero-, straight-chained, branched, cyclic, saturated and unsaturated aliphatic radicals; and substituted, unsubstituted, and hetero-aromatic radicals;

$R_3$ is selected from the group consisting of substituted, unsubstituted, hetero-, straight-chained, branched, cyclic, saturated and unsaturated aliphatic radicals; and substituted, unsubstituted, and hetero-aromatic radicals;

$R_2$, $R_4$, and $R_7$ are independently selected from the group consisting of hydrogen; substituted, unsubstituted, hetero-, straight-chained, branched, cyclic, saturated and unsaturated aliphatic radicals; and substituted, unsubstituted, and hetero-aromatic radicals;

$R_6$ is selected from the group consisting of substituted, unsubstituted, hetero-, straight-chained and branched aliphatic radicals;

$L_1$ is an optional linkage connecting A to B and, if present, comprises a disulfide, poly(ethylene glycol), methoxy-poly(ethylene glycol), poly(ethylene oxide), polypropylene glycol), poly(tetramethylene glycol), poly(ethylene oxide-co-propylene oxide), or a copolymer thereof;

X is a biobeneficial agent selected from the group consisting of poly(alkylene glycols), methoxypoly(ethylene glycol), poly(N-vinyl pyrrolidone), poly(acrylamide methyl propane ulfonic acid), poly(styrene sulfonate), sulfonated dextran, polyphosphazenes, poly(orthoesters), poly(tyrosine carbonate), hyaluronic acid, heparin, a graft copolymer of poly(L-lysine) and poly(ethylene glycol), and salts, copolymers and combinations thereof; a free radical scavenger, a nitric oxide donor, rapamycin, tacrolimus, paclitaxel, docetaxel, estradiol, clobetasol, idoxifene, tazarotene, and salts and combinations thereof; antiproliferatives, antineoplastics, antimitotics, anti-inflammatories, antiplatelets, anticoagulants, antifibrins, antithrombins, antibiotics, antiallergics, antioxidants, and salts and combinations thereof; 40-O-(2-hydroxy)ethyl-rapamycin (everolimus), 40-O-(3-hydroxypropyl)-rapamycin, 40-O-[2-(2-hydroxy)ethoxy]ethyl-rapamycin, and salts and combinations thereof;

$L_2$ is a linkage connecting X to the polymer; and n and m are independently integers not equal to 0.

6. The stent of claim 5, wherein $L_1$ is absent.

7. The stent of claim 5, wherein X is selected from the group consisting of poly(alkylene glycols), poly(N-vinyl pyrrolidone), poly(acrylamide methyl propane sulfonic acid), poly(styrene sulfonate), sulfonated dextran; polyphosphazenes, poly(orthoesters), poly(tyrosine carbonate), hyaluronic acid, heparin, poly(ethylene glycol), a graft copolymer of poly(L-lysine) and poly(ethylene glycol), and salts, copolymers and combinations thereof; a free radical scavenger, a nitric oxide donor, rapamycin, everolimus, tacrolimus, paclitaxel, docetaxel, estradiol, clobetasol, idoxifene, tazarotene, and salts and combinations thereof.

8. The stent of claim 5, wherein X is a free radical scavenger selected from the group consisting of 2,2',6,6'-tetramethyl-1-piperinyloxy, free radical; 4-amino-2,2',6,6'-tetramethyl-1-piperinyloxy, free radical; 4-hydroxy-2,2',6,6'-tetramethyl-piperidene-1-oxy, free radical; 2,2',3,4,5,5'-hexamethyl-3-imidazolinium-1-yloxy methyl sulfate, free radical; 16-doxyl-stearic acid, free radical; superoxide dismutase mimic; and salts and combinations thereof.

9. The stent of claim 5, wherein X is a nitric oxide donor selected from the group consisting of S-nitrosothiols, nitrites, N-oxo-N-nitrosamines, substrates of nitric oxide synthase, diazenium diolates and salts and combinations thereof.

10. The stent of claim 5, wherein X is selected from the group consisting of antiproliferatives, antineoplastics, antimitotics, anti-inflammatories, antiplatelets, anticoagulants, antifibrins, antithrombins, antibiotics, antiallergics, antioxidants, and salts and combinations thereof.

11. The stent of claim 5, wherein X is rapamycin, tacrolimus, 40-O-(2-hydroxy)ethyl-rapamycin (everolimus), 40-O-(3-hydroxypropyl)-rapamycin, or 40-O-[2-(2-hydroxy)ethoxy]ethyl-rapamycin.

12. The stent of claim 5, wherein $L_2$ is selected from the group consisting of amides, esters, anhydrides, ketals, acetals, orthoesters and all-aromatic carbonates.

13. The stent of claim 5, wherein X is poly(ethylene glycol) or methoxypoly(ethylene glycol).

* * * * *